United States Patent
Cao et al.

(10) Patent No.: US 6,228,855 B1
(45) Date of Patent: May 8, 2001

(54) AROMATIC ESTERS OF CAMPTOTHECINS AND METHODS TO TREAT CANCERS

(75) Inventors: Zhisong Cao, Friendswood; Beppino C. Giovanella, Houston, both of TX (US)

(73) Assignee: The Stehlin Foundation for Cancer Research, Houston, TX (US)

( * ) Notice: Subject to any disclaimer, the term of this patent is extended or adjusted under 35 U.S.C. 154(b) by 0 days.

(21) Appl. No.: 09/365,633

(22) Filed: Aug. 3, 1999

(51) Int. Cl.⁷ ............... A61K 31/436; A61K 31/437; C07D 401/14; C07D 407/14; C07D 487/14
(52) U.S. Cl. ............... 514/224.2; 514/185; 546/48; 546/50; 546/51
(58) Field of Search ............... 546/48, 50, 51; 514/185, 224.2

(56) References Cited

U.S. PATENT DOCUMENTS

| | | |
|---|---|---|
| Re. 32,518 | 10/1987 | Miyasaka et al. . |
| 3,894,029 | 7/1975 | Winterfeldt et al. . |
| 4,399,282 | 8/1983 | Miyasaka et al. . |
| 4,473,692 * | 9/1984 | Miyasaka et al. ........... 546/48 |
| 4,604,463 * | 8/1986 | Miyasaka et al. ........... 544/125 |
| 4,894,456 | 1/1990 | Wall et al. . |
| 4,914,205 | 4/1990 | Sawada et al. . |
| 4,943,579 | 7/1990 | Vishnuvajjala . |
| 5,053,512 | 10/1991 | Wani et al. . |
| 5,106,742 | 4/1992 | Wall et al. . |
| 5,126,351 | 6/1992 | Luzzio et al. . |
| 5,180,722 | 1/1993 | Wall et al. . |
| 5,225,404 | 7/1993 | Giovanella et al. . |
| 5,227,380 * | 7/1993 | Wall et al. ............... 514/253 |
| 5,352,789 | 10/1994 | Hinz . |
| 5,391,745 | 2/1995 | Danishefsky et al. . |
| 5,466,047 | 11/1995 | Danishefsky et al. . |
| 5,525,731 | 6/1996 | Danishefsky et al. . |
| 5,541,327 | 7/1996 | Danishefsky et al. . |
| 5,552,154 | 9/1996 | Giovanella et al. . |
| 5,552,156 | 9/1996 | Burke . |
| 5,646,159 | 7/1997 | Wall . |
| 5,652,244 | 7/1997 | Giovanella et al. . |
| 5,731,316 * | 3/1998 | Cao et al. ............... 514/283 |
| 5,736,156 | 4/1998 | Burke . |
| 5,756,512 | 5/1998 | Johnson . |
| 5,786,344 | 7/1998 | Ratain et al. . |
| 5,801,167 | 9/1998 | Bedeschi et al. . |
| 5,834,012 | 11/1998 | Perez-Soler et al. . |
| 5,837,673 | 11/1998 | Tsujihara et al. . |
| 5,840,899 | 11/1998 | Bedeschi et al. . |
| 5,840,900 | 11/1998 | Greenwald et al. . |
| 5,856,333 | 1/1999 | Cabri et al. . |
| 5,859,022 | 1/1999 | Hausheer et al. . |
| 5,859,023 | 1/1999 | Hausheer et al. . |
| 5,880,131 | 3/1999 | Greenwald et al. . |
| 5,880,133 | 3/1999 | Hausheer et al. . |
| 5,882,679 | 3/1999 | Needham . |
| 5,892,043 | 4/1999 | Tsujihara et al. . |
| 5,900,419 | 5/1999 | Hausheer et al. . |
| 5,908,835 | 6/1999 | Bissery . |
| 5,910,491 | 6/1999 | Hausheer et al. . |
| 6,111,107 | 8/2000 | Greenwald et al. ........... 546/48 |

FOREIGN PATENT DOCUMENTS

| | | |
|---|---|---|
| 30 26 172 | 2/1981 | (DE) . |
| 0074256 * | 3/1983 | (EP) . |
| 0 538 534 | 4/1993 | (EP) . |
| 56-108787 | 8/1981 | (JP) . |
| 64-61482 | 3/1989 | (JP) . |
| WO 92/05785 | 4/1992 | (WO) . |
| WO 94/19353 | 9/1994 | (WO) . |
| WO 96/02546 A1 | 7/1995 | (WO) . |
| WO 97-28165 | 8/1997 | (WO) . |
| WO 97/28165 | 8/1997 | (WO) . |
| WO 98/07713 | 8/1997 | (WO) . |

OTHER PUBLICATIONS

Tetrahedron Letters, A.V. Rama Rao et al, vol. 35, No. 21, pp. 3613–3616, Mar. 1994.*

CAPLUS 121:109357, RN #156969–70, Mar. 1994.*

Wall et al J.of Med. Chem. 1993 vol. 36 pp. 2689–2700, Feb. 1993.*

Wu, et al., *Phytochemistry*, vol. 39, No. 2. pp. 383–385, 1995.

Fessenden et al., "Techniques and Experiments for Organic Chemistry," PWS Publishers, 1983, ISBN 0–8175–0755–2, pp. 56–59.

(List continued on next page.)

*Primary Examiner*—Alan L. Rotman
*Assistant Examiner*—Rita Desai
(74) *Attorney, Agent, or Firm*—Kilyk & Bowersox, P.L.L.C.

(57) ABSTRACT

Aromatic camptothecin ester compounds having the formula:

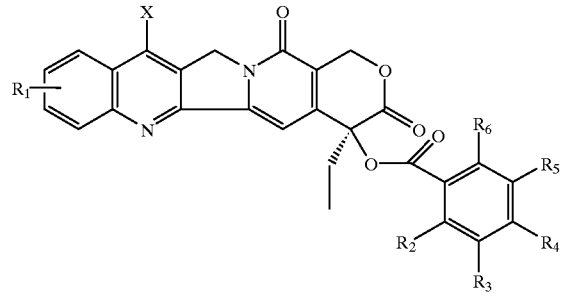

are described as well as formulations containing the compounds. Methods of treating cancer and/or tumors are also disclosed.

107 Claims, No Drawings

OTHER PUBLICATIONS

Van Nostrand's Scientific Encyclopedia 7th Ed. (vol. 1)(1989), pp. 625–627.
McGraw Hill Encyclopedia of Science and Technology, vol. 3, 5th Ed., 1982, pp. 142–146.
Wani et al., *J. Med. Chem.*, vol. 23, pp. 554–560, 1980.
Wani et al., *J. Med. Chem.*, vol. 29, pp. 2358–2363, 1986.
Wall et al., *J. Med. chem.*, vol. 29, pp. 1553–1555, 1986.
Akimoto et al., *J. Chromatography*, vol. 588, pp. 165–170, 1991.
Gunasekera et al., *J. Natural Products (Lloydia)*, vol. 42, No. 5, pp. 475–477, 1979.
Sakato et al., *Agricultural and Biological chemistry*, vol. 38, No. 1, pp. 217–218, 1974.
Barilero et al., *J. Chromatography*, vol. 575, pp. 275–280 (1992).
Giovanella et al., *Science*, vol. 246, pp. 1046–1048, Nov. 24, 1989.
Adamovics, *Chem. Absts.*, vol. 92, entry 59061 (1980).
Yakult, *Chem. Absts.*, vol. 101, entry 91319d (1984).
Yakult, *Chem. Absts.*, vol. 101, entry 91322z (1984).
Wu, *Chem. Absts.*, vol. 123,, entry 52308 (1995).
Wall and Wani, *Nat. Prod. and Drug Dev.*, Munksgaard, Copenhagen, 1984.
Adamovics, *Phytochemistry*, vol. 18, pp. 1085–1086, 1979.
Database WPI (Week 8946); AN 89–335912; pp. 1–2, Derwent Publications Ltd., London, GB; XP002033248; Abstract of JP 01 249 777a (Yakult Honsha K.K.) Oct. 5, 1989.
Database WPI (Week 9347); AN 93–374594; pp. 1–2, Derwent Publications Ltd., London, GB; XP002033249; Abstract of JP 05 279 370 A (Daiichi Pharm. Co., Ltd. & Hakult Honsha K.K.) Oct. 26, 1993.
Database WPI (Week 8945); AN 89–329502; pp. 1–2; Derwent Publications Ltd., London, GB; XP002033250; Abstract of JP 01 246 287 A (Yakult Honsha K.K.) Oct. 2, 1989.
Wall et al., "Plant Antitumor Agents. 30, Synthesis and Structure Activity of Novel Camptothecin Analogs," *J. Med. Chem.*, vol. 36, No. 18, pp. 2689–2700, 1993.
International Search Report for PCT/US97/01728 dated Jul. 15, 1997.
International Search Report for PCT/US00/20133 mailed Dec. 7,2000.
Rao et al., "Regloselective Synthesis of Camptothecin"Tetrahedron Letters, vol. 35, No. 21, pp. 3613–3616 (May. 23, 1994).

* cited by examiner

AROMATIC ESTERS OF CAMPTOTHECINS AND METHODS TO TREAT CANCERS

FIELD OF THE INVENTION

The present invention is directed to aromatic esters of camptothecins.

BACKGROUND OF THE INVENTION

Camptothecin, a natural product originally found in China, but now grown in many countries, was isolated and purified by Wall and his coworkers in 1966 (J. Am. Chem. Soc. 88, 3888, 1966). This compound was initially tested against the mouse leukemia L 1210 system and showed good activity. Since it proved to be a potent anticancer in animal models, camptothecin was quickly tested in human clinical trials. At this time, unfortunately, anticancer activity was not found; instead, severe toxicity was observed for those patients who participated in the trials (Gottlieb et al, Cancer Chemother. Rep. 54, 461, 1970, and 56, 103, 1972, Muggia et al, Cancer Chemother. Rep. 56, 515, 1972, Moertel et al, Cancer Chemother. Rep. 56, 95, 1972, and Schaeppi et al, Cancer Chemother. Rep. 5:25, 1974). Trials were accordingly discontinued. The reason for the failure of the early trial was later found to be an incorrect drug formulation selected. Camptothecin is insoluble in water itself. In order to use the drug for i.v. administration, camptothecin was converted to its sodium form (CPT sodium carboxylate). This form although water-soluble, is practically devoid of anticancer activity, and quite toxic. For example, a careful evaluation of these agents in animal models made by Wani et al revealed that the sodium salt is only 10–20% as potent as the parent camptothecin (J. Med. Chem. 23, 554, 1980). In addition, important parameters for anticancer activity in the camptothecin series have now been established (Wall et al., Ann. Rev. Pharmacol. Toxicol. 17, 117, 1977). The intact lactone form with an α-hydroxyl group at the position 20 of the molecule is believed to be essential for antitumor activity.

Keeping the molecule as an intact lactone form is the key for success of the treatment. In the laboratory, camptothecin and its derivatives have shown a promising activity against a wide spectrum of human tumors grown in xenografts in nude mice (Giovanella et al., Cancer Res. 51, 3052, 1991, and Natelson et al., Annals N.Y. Acad. Sci. 803, 224, 1996), but much less activity was observed in human clinical trials. This difference in antitumor activity has been associated with the finding that the hydrolysis of lactone to carboxylate of the molecule is much faster in human plasma than in mouse. For example, about 50% of 9-nitrocamptothecin is present as lactone form in mice plasma, but only 5% of the molecule can be found as the lactone form in human plasma. The lactone camptothecin molecule is not stable in human. More studies on the stability of camptothecin derivatives in human serum have been conducted by Burke et al. (Annals N.Y. Acad. Sci. 803, 29. 1996).

Clearly, there is a need to obtain a camptothecin compound that keeps the molecule as an intact lactone when it is in circulation in the body. In other words, a camptothecin product having longer biological life span is wanted. A number of attempts have been made to obtain protected camptothecin derivatives, but none of the compounds has been disclosed to significantly increase the biological life span. U.S. Pat. No. 4,943,579 relates to the preparation of several water-soluble camptothecin esters by the esterification of camptothecin with amino acids as acylating reagents at the 20 position. U.S. Pat. No. 5,646,159 relates to the esterification of 10,11-dioxymethylenecamptothecin with amino acid derivatives as acylating reagents at the position 20 to provide several water-soluble compounds. These two patents use the same acylating reagents (amino acids) for the esterification reaction, and the products are water-soluble, thus they are not related to water-insoluble camptothecin esters and are not within the scope of the present invention. U.S. Pat. No. 5,731,316 discloses esterification of camptothecins with various different acylating reagents rather than amino acids to provide a wide range water-insoluble ester compounds of camptothecins. The compounds disclosed in this invention significantly increase the biological life span while maintaining the inherent antitumor activity and lowering the toxicity. However, the previous patent did not use any aromatic functionality for the esterification reaction. The present invention relates, for the first time, to making aromatic esters of camptothecins.

SUMMARY OF THE INVENTION

Accordingly, it is an object of the present invention to provide new camptothecin compounds which are active against various types of tumors and are non-toxic.

It is a further object of the present invention to provide aromatic esters of camptothecins.

It is another object of the present invention to provide the prodrugs of camptothecins. These prodrugs can regenerate to the parent active camptothecin compounds by an enzymatic hydrolysis after in vivo administration.

It is still another objection of the present invention to provide the methodology of preparing the above-described aromatic esters of camptothecins.

It is still a further object of the present invention to provide an improved treatment for certain types of cancers.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a compound of formula (I).

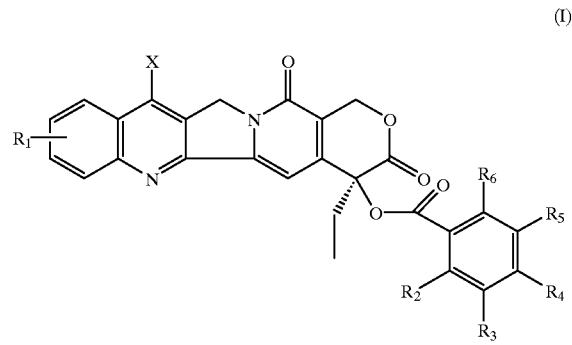

The present invention also relates to a method for treating malignant tumors or cancer in a mammal and comprises administering an effective amount of a composition containing one or more of the compounds of formula (I) depicted above.

DETAILED DESCRIPTION OF THE INVENTION

The present invention relates to novel camptothecin derivatives. These camptothecin derivatives are preferably water-insoluble aromatic camptothecin esters. The aromatic camptothecin esters preferably have the formula (I):

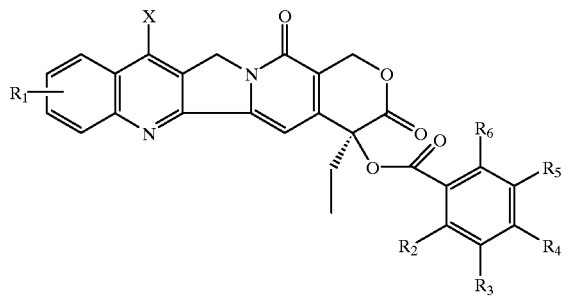

In this formula, the various R groups represent substituents on one of the rings of the structure above. In particular, $R^1$ represent H, $NO_2$, $NH_2$, $N_3$, a halogen (e.g., F, Cl, Br, I), carboxyl (COOH), a $C_{1-16}$ alkyl group, $C_{1-16}$ alkylenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$ (where $R^7$ is H, or a $C_{1-8}$ alkyl group, n is an integer of from 1 to about 8), hydroxyl, SH, $SR^8$ (where $R^8$ is a $C_{1-8}$ alkyl group, or a phenyl group, or a substituted phenyl group), a carbonyl group, (e.g., $COR^9$, where $R^9$ is a $C_{1-8}$ alkyl group, or a phenyl group, or a substituted phenyl group), a $SiR_3^{10}$ (where $R^{10}$ is a $C_{1-4}$ alkyl group). The $R^1$ group is respectively positioned at the 9, or 10, or 1 1, or 12 position of ring A. $R^1$ can also be a disubstituted 10, 11—O—$(CH_2)_y$—O— group (where y is an integer of from 1 to 3). X represents H, a $C_{1-8}$ alkyl group, a $C_{1-8}$ alkenyl group, a $C_{1-8}$ alkoxyl group, an aroxyl group, a $SiR_3^{11}$ group (where $R^{11}$ is a $C_{1-4}$ alkyl group), or $CH_2NZY$ where Z and Y are, independently, H, $C_{1-4}$ alkyl, or a $C_{1-4}$ halogenated alkyl group. $R^2$, $R^3$, $R^4$, $R^5$, and $R^6$ are, independently, H(s), $C_{1-2}$ alkyl group(s), $C_{1-12}$ alkenyl group(s), COOH(s), $SO_3H$(s), CN(s), $CF_3$(s), $CCl_3$(s), $CH_2F$(s), $CH_2Cl$(s), $CHF_2$(s), $CHCl_2$(s), OH(s), $OR^{12}$(s) (where $R^{12}$ is a $C_{1-8}$ alkyl group, or a $C_{1-8}$ alkenyl group, or an aromatic group), $N_3$, $NO_2$(s), $NR_2^{13}$(s) (where $R^{13}$ is H, or $C_{1-4}$ alkyl group), carbonyl group (s), halogen(s).

More preferred aromatic camptothecin esters of the present invention are as follows, wherein:

| | |
|---|---|
| $R^2 = R^3 = R^4 = R^5 = R^6 = H$; | $R^2 = R^3 = R^5 = R^6 = H, R^4 = CF_3$; |
| $R^2 = R^3 = R^4 = R^6 = H, R^5 = CF_3$; | $R^2 = R^3 = R^4 = R^5 = H, R^6 = CF_3$; |
| $R^2 = R^3 = R^6 = H, R^4 = R^5 = NO_2$; | $R^2 = R^4 = R^6 = H, R^3 = R^5 = NO_2$; |
| $R^2 = R^3 = R^5 = H, R^4 = R^6 = NO_2$; | $R^2 = R^3 = R^5 = R^6 = H, R^4 = NO_2$; |
| $R^2 = R^3 = R^4 = R^6 = H, R^5 = NO_2$; | $R^3 = R^4 = R^5 = R^6 = H, R^2 = NO_2$; |
| $R^3 = R^4 = R^5 = R^6 = H, R^2 = CN$; | $R^2 = R^3 = R^4 = R^6 = H, R^5 = CN$; |
| $R^2 = R^3 = R^5 = R^6 = H, R^4 = CN$; | $R^3 = R^4 = R^5 = R^6 = H, R^2 = F$; |
| $R^2 = R^3 = R^4 = R^6 = H, R^5 = F$; | $R^2 = R^3 = R^5 = R^6 = H, R^4 = F$; |
| $R^3 = R^4 = R^5 = R^6 = H, R^2 = Cl$; | $R^2 = R^3 = R^4 = R^6 = H, R^5 = Cl$; |
| $R^2 = R^3 = R^5 = R^6 = H, R^4 = Cl$; | $R^3 = R^4 = R^5 = R^6 = H, R^2 = Br$; |
| $R^2 = R^3 = R^4 = R^6 = H, R^5 = Br$; | $R^2 = R^3 = R^5 = R^6 = H, R^4 = Br$; |
| $R^3 = R^4 = R^5 = R^6 = H, R^2 = OH$; | $R^2 = R^3 = R^4 = R^6 = H, R^5 = OH$; |

$R^2=R^3=R^5=R^6=H$, $R^4=OH$. Preferably for these above-mentioned preferred compounds, $R^1$ is hydrogen and X represents hydrogen as well.

Another group of preferred compounds are the following, wherein:

| | |
|---|---|
| $R^2 = R^3 = R^4 = R^5 = R^6 = H$; | $R^2 = R^3 = R^5 = R^6 = H, R^4 = CF_3$; |
| $R^2 = R^3 = R^4 = R^6 = H, R^5 = CF_3$; | $R^2 = R^3 = R^4 = R^5 = H, R^6 = CF_3$; |
| $R^2 = R^3 = R^6 = H, R^4 = R^5 = NO_2$; | $R^2 = R^4 = R^6 = H, R^3 = R^5 = NO_2$; |
| $R^2 = R^3 = R^5 = H, R^4 = R^6 = NO_2$; | $R^2 = R^3 = R^5 = R^6 = H, R^4 = NO_2$; |
| $R^2 = R^3 = R^4 = R^6 = H, R^5 = NO_2$; | $R^3 = R^4 = R^5 = R^6 = H, R^2 = NO_2$; |
| $R^3 = R^4 = R^5 = R^6 = H, R^2 = CN$; | $R^2 = R^3 = R^4 = R^6 = H, R^5 = CN$; |
| $R^2 = R^3 = R^5 = R^6 = H, R^4 = CN$; | $R^3 = R^4 = R^5 = R^6 = H, R^2 = F$; |
| $R^2 = R^3 = R^4 = R^6 = H, R^5 = F$; | $R^2 = R^3 = R^5 = R^6 = H, R^4 = F$; |
| $R^3 = R^4 = R^5 = R^6 = H, R^2 = Cl$; | $R^2 = R^3 = R^4 = R^6 = H, R^5 = Cl$; |
| $R^2 = R^3 = R^5 = R^6 = H, R^4 = Cl$; | $R^3 = R^4 = R^5 = R^6 = H, R^2 = Br$; |
| $R^2 = R^3 = R^4 = R^6 = H, R^5 = Br$; | $R^2 = R^3 = R^5 = R^6 = H, R^4 = Br$; |
| $R^3 = R^4 = R^5 = R^6 = H, R^2 = OH$; | $R^2 = R^3 = R^4 = R^6 = H, R^5 = OH$; |
| $R^2 = R^6 = H, R^3 = R^5 = NO_2$, $R^4 = CH_3$; | |
| $R^2 = R^3 = R^4 = R^6 = H, R^5 = OH$; | $R^2 = R^3 = R^5 = R^6 = H, R^4 = OH$. |

For the above second group of preferred compounds, $R^1$ is preferably 9-$NO_2$ and X represents hydrogen.

Another group of preferred compounds are the following, wherein:

| | |
|---|---|
| $R^2 = R^3 = R^4 = R^5 = R^6 = H$; | $R^2 = R^3 = R^5 = R^6 = H, R^4 = CF_3$; |
| $R^2 = R^3 = R^4 = R^6 = H, R^5 = CF_3$; | $R^2 = R^3 = R^4 = R^5 = H, R^6 = CF_3$; |
| $R^2 = R^3 = R^6 = H, R^4 = R^5 = NO_2$; | $R^2 = R^4 = R^6 = H, R^3 = R^5 = NO_2$; |
| $R^2 = R^3 = R^5 = H, R^4 = R^6 = NO_2$; | $R^2 = R^3 = R^5 = R^6 = H, R^4 = NO_2$; |
| $R^2 = R^3 = R^4 = R^6 = H, R^5 = NO_2$; | $R^3 = R^4 = R^5 = R^6 = H, R^2 = NO_2$; |
| $R^3 = R^4 = R^5 = R^6 = H, R^2 = CN$; | $R^2 = R^3 = R^4 = R^6 = H, R^5 = CN$; |
| $R^2 = R^3 = R^5 = R^6 = H, R^4 = CN$; | $R^3 = R^4 = R^5 = R^6 = H, R^2 = F$; |
| $R^2 = R^3 = R^4 = R^6 = H, R^5 = F$; | $R^2 = R^3 = R^5 = R^6 = H, R^4 = F$; |
| $R^3 = R^4 = R^5 = R^6 = H, R^2 = Cl$; | $R^2 = R^3 = R^4 = R^6 = H, R^5 = Cl$; |
| $R^2 = R^3 = R^5 = R^6 = H, R^4 = Cl$; | $R^3 = R^4 = R^5 = R^6 = H, R^2 = Br$; |
| $R^2 = R^3 = R^4 = R^6 = H, R^5 = Br$; | $R^2 = R^3 = R^5 = R^6 = H, R^4 = Br$; |
| $R^3 = R^4 = R^5 = R^6 = H, R^2 = OH$; | $R^2 = R^3 = R^4 = R^6 = H, R^5 = OH$; |

$R^2=R^3=R^5=R^6=H$, $R^4=OH$. For this third group of preferred compounds, $R^1$ is preferably 9-$NH_2$ and X represents hydrogen.

For the above-described substitutents, preferred alkyl groups are —$CH_3$, —$CH_2CH_3$, $CH_3CH_2CH_2$—, $CH_3(CH_2)_3$—, $CH_3(CH_2)_4$—, $CH_3(CH_2)_5$—, and $CH_3(CH_2)_{6-17}$—, $(CH_3)_2CH$—, $CH_3$—$CH_3$—$CH_2CH$—$CH_3$, $(CH_3CH_2)_2CH$—, $(CH_3CH_2CH_2)_2CH$—, $(CH_3)_3C$—, $CH_3(CH_3CH_2)_2C$—, Preferred alkylenyl groups are $CH_2=CH$—, $CH_3CH=CH$—, $CH_3CH=C(CH_3)$—, $CH_3CH=CHCH_2$—, $CH_3CH_2CH=CHCH_2$—, $CH_3(CH_2)_{3-15}CH=CH$—, $CH_3CH=CH$—$(CH_2)_{3-15}CH_2$, $CH_2=CH$—$CH=CH$—, $CH_3CH=CH$—$CH=CH$—, $CH_3(CH_2)_{3-6}$—$CH=CH$—$CH=CH$—$(CH_2)_{3-6}$—$CH_2$—, Preferred $C_{3-8}$ cycloalkyl groups are

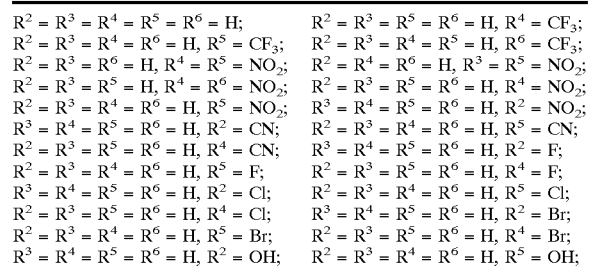

Preferred $C_{1-8}$ alkoxyl groups are MeO—, EtO—, n—$C_3H_7$—, i—$C_3H_7$—O—, n—$C_4H_9$—O—, i—$C_4H_9$——O—, t—$C_4H_4$—O—, n—$C_5$—$H_{11}$O—, $(CH_3)_2CHCH_2CH_2O$—,

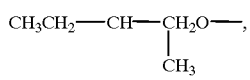

(CH₃C₂)₂CH—O—, n—CH₆H₁₃—O—, n—C₇H₁₅—O—, n—C₈H₁₇—O—.

Preferred aroxyl groups are p—CH₃OC₆H₄—, m—CH₃O—C₆H₄—, o—CH₃OC₆H₄—, o,p-Dimethoxyl phenyl-, m,m-Dimethoxyl phenyl-, m,p-Dimethoxyl phenyl-, o—CH₃CH₂OC₆H₄—, m—CH₃CH₂OC₆H₄—, p—CH₃CH₂O—C₆H₄—, Preferred cycloalkyl groups are cyclo-$C_3$, cyclo-$C_4$, cyclo-$C_5$, cyclo-$C_6$, cyclo-$C_7$, cyclo-$C_8$, alkyl substituted cyclo-$C_3$, alkyl substituted cyclo-$C_4$, alkyl substituted cyclo-$C_5$, alkyl substituted cyclo-$C_6$, alkyl substituted cyclo-$C_7$, and alkyl substituted cyclo-$C_8$ (where alkyl includes preferably those alkyl groups described above).

Preferred unsubstituted and substituted phenyl groups are $C_6H_5$—, (o,m,p) $CH_3C_6H_4$—, halogen substituted phenyl groups (X $C_6H_4$, wherein X=F, Cl, Br, I), (o,p,m) $CH_3OC_6H_4$—, (o,m,p) $NO_2C_6H_4$—, (o,m,p) $NH_2C_6H_4$—, (o,m,p) $CNC_6H_4$—, Preferred carbonyl groups are

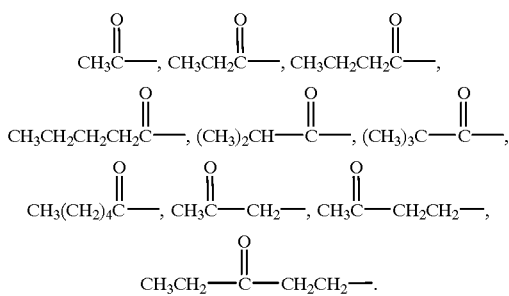

Conversion of the prodrugs to camptothecins is mediated by a group of enzymes called esterases. Mammalian carboxylesterases represent a multigene family and are present in a wide variety of organs and tissues of many mammalian species (Satoh, in reviews in Biochemical Toxicology, 8:155–81, New York: Elsevier, 1987; Heymann, in Enzymatic Basis of Detoxication, 2:291–323, New York: Academic, 1980, and in Metabolic Basis of Detoxication, 1:229–45, New York: Academic, 1982). In general, the highest hydrolase activity occurs in the liver. Carboxylesterase activity is present in many tissues in addition to liver. More information about distribution of carboxylesterases in tissues can be found in a review article written by Satoh et al. (Annu. Rev. Pharmacol. Toxicol. 38, 257, 1998). Carboxylesterases are known to be responsible for the hydrolysis of many exogenous compounds, the consequences of which include both activation of prodrugs and deactivation of drugs. CPT-11, a semisynthetic camptothecin derivative and now commercially available for cancer treatment, is a prodrug of SN-38. This compound is converted to SN-38 by carboxylesterases (Danks et al., Cancer Res. 58, 20, 1998; Potter et al., Cancer Res. 58, 2646, 1998; Tsuji et al., J. Pharmacobio-Dyn. 14, 341, 1991). The prodrugs disclosed by the present invention are rapidly distributed throughout the body within a short period of time after delivery and are then converted to active camptothecin compounds by carboxylesterases specifically in tissues.

The prodrugs of the present invention are prepared by esterifying the 20-hydroxyl group of camptothecins with the corresponding aromatic carboxylic acids. The reaction can be done in DMF (N,N-dimethylformamide, Aldich, Milwaukee, Wis.) with DCC (1,3-dicyclohexylcarbodiimide, Aldrich, Milwaukee, Wis.) as catalyst as depicted in Scheme 1.

Scheme 1

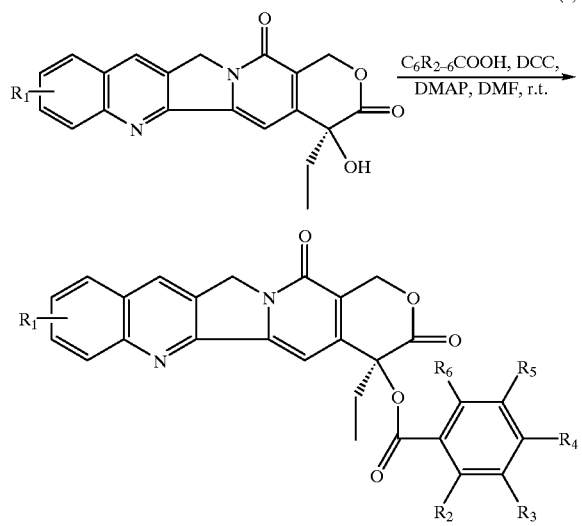

From among these formulae, preferred structures represented by formula 1 are as follows:

CZ176:

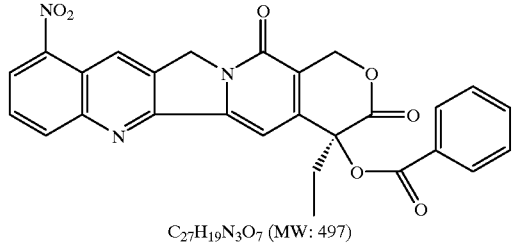

$C_{27}H_{19}N_3O_7$ (MW: 497)

CZ185:

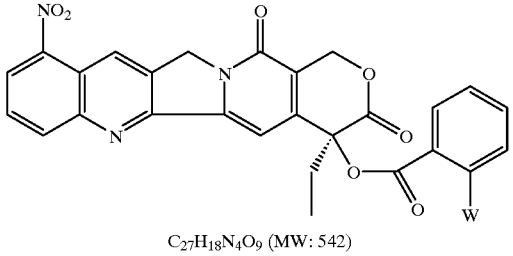

$C_{27}H_{18}N_4O_9$ (MW: 542)

CZ188:

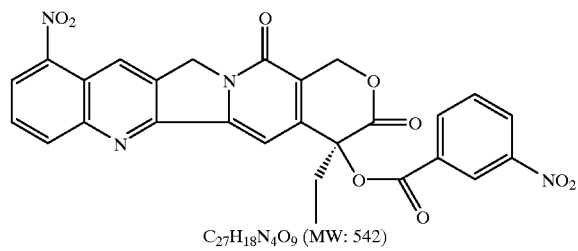

$C_{27}H_{18}N_4O_9$ (MW: 542)

CZ189:
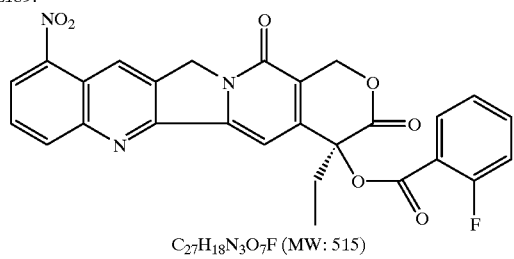
$C_{27}H_{18}N_3O_7F$ (MW: 515)
CZ190:
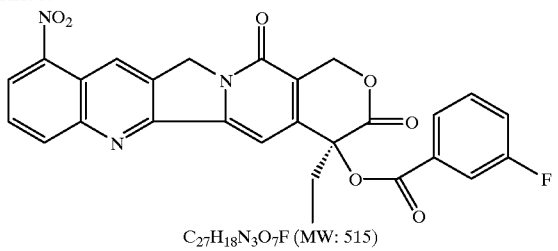
$C_{27}H_{18}N_3O_7F$ (MW: 515)
CZ192:
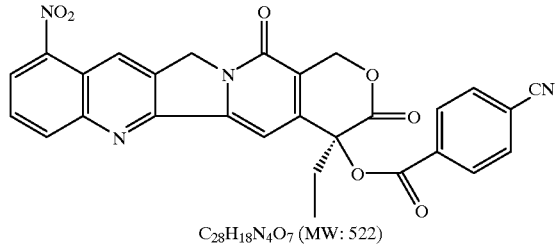
$C_{28}H_{18}N_4O_7$ (MW: 522)
CZ196:
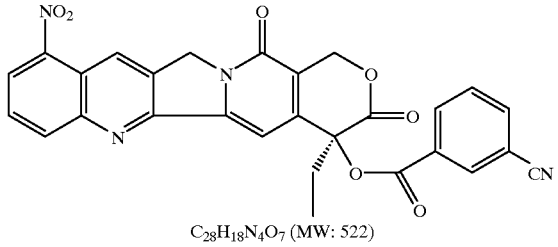
$C_{28}H_{18}N_4O_7$ (MW: 522)
CZ197:
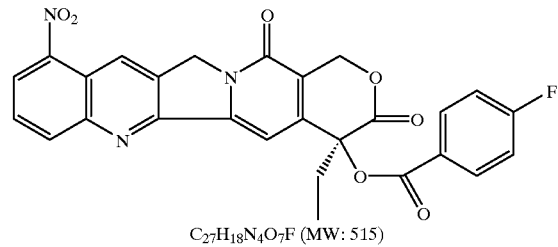
$C_{27}H_{18}N_4O_7F$ (MW: 515)
CZ198:
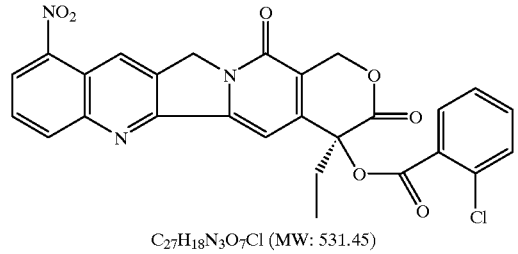
$C_{27}H_{18}N_3O_7Cl$ (MW: 531.45)
CZ199:
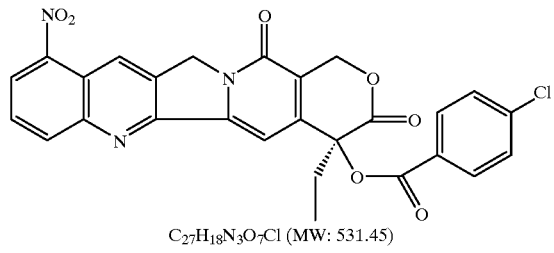
$C_{27}H_{18}N_3O_7Cl$ (MW: 531.45)
CZ200:
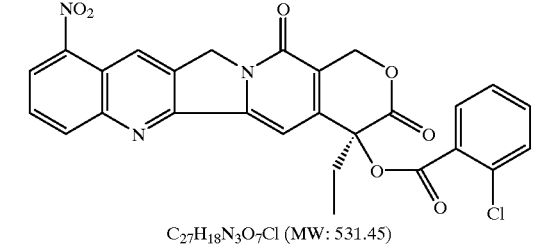
$C_{27}H_{18}N_3O_7Cl$ (MW: 531.45)
CZ201:
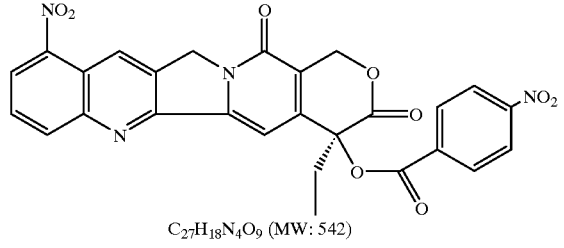
$C_{27}H_{18}N_4O_9$ (MW: 542)
CZ202:
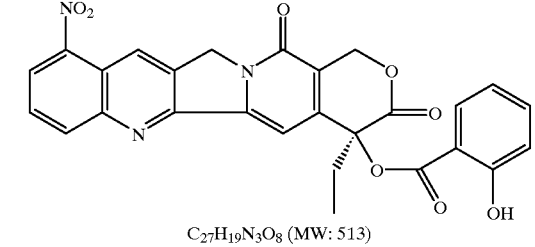
$C_{27}H_{19}N_3O_8$ (MW: 513)
CZ203:
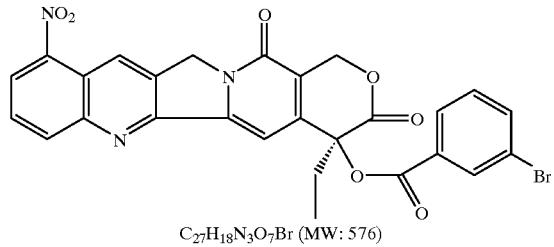
$C_{27}H_{18}N_3O_7Br$ (MW: 576)
CZ204:
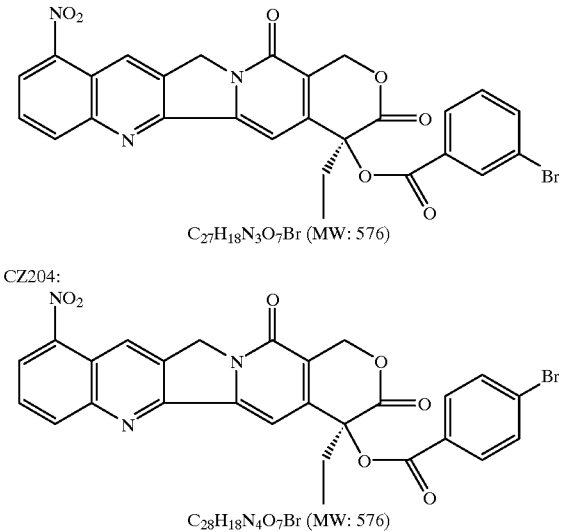
$C_{28}H_{18}N_4O_7Br$ (MW: 576)

CZ208:
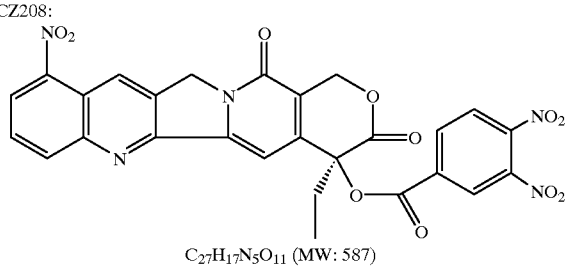
$C_{27}H_{17}N_5O_{11}$ (MW: 587)
CZ209:
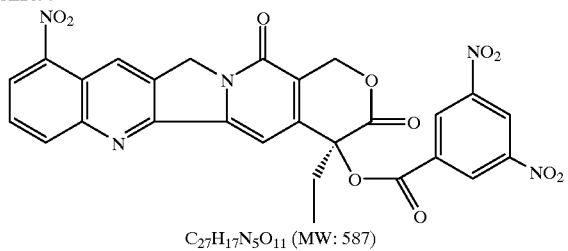
$C_{27}H_{17}N_5O_{11}$ (MW: 587)
CZ212:
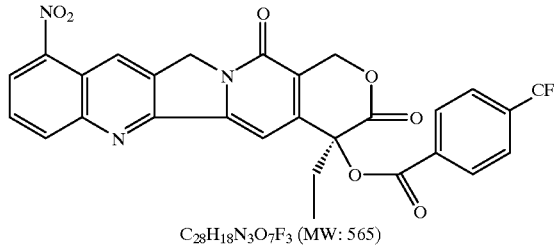
$C_{28}H_{18}N_3O_7F_3$ (MW: 565)
CZ213:
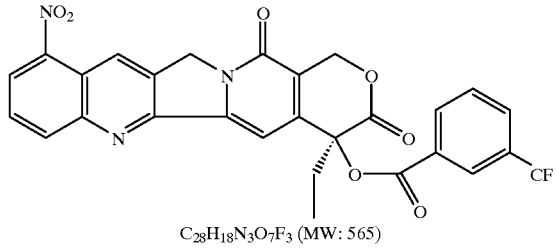
$C_{28}H_{18}N_3O_7F_3$ (MW: 565)
CZ215:
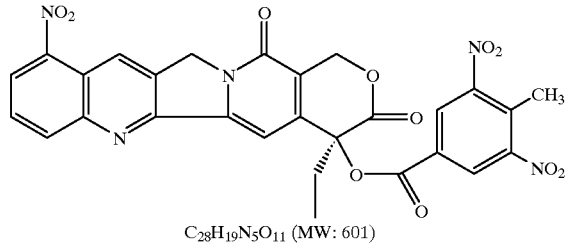
$C_{28}H_{19}N_5O_{11}$ (MW: 601)
CZ216:
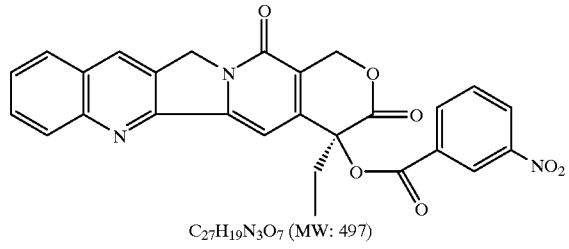
$C_{27}H_{19}N_3O_7$ (MW: 497)
CZ217:
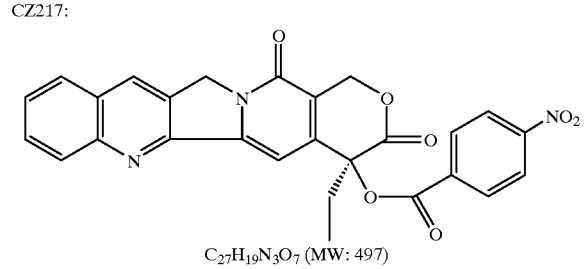
$C_{27}H_{19}N_3O_7$ (MW: 497)
CZ218:
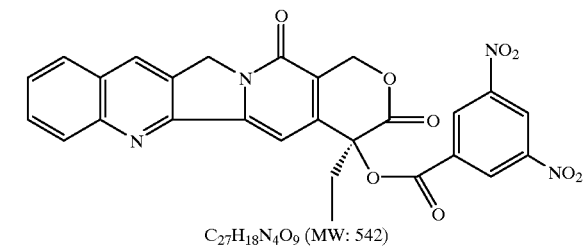
$C_{27}H_{18}N_4O_9$ (MW: 542)
CZ219:
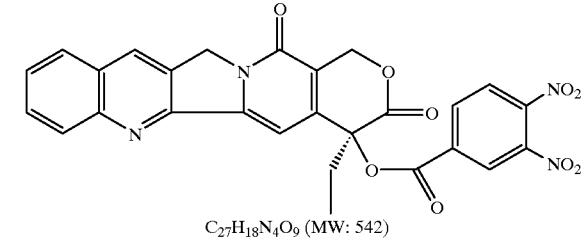
$C_{27}H_{18}N_4O_9$ (MW: 542)
CZ220:
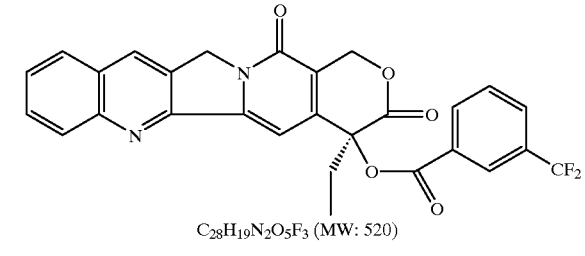
$C_{28}H_{19}N_2O_5F_3$ (MW: 520)
CZ221:
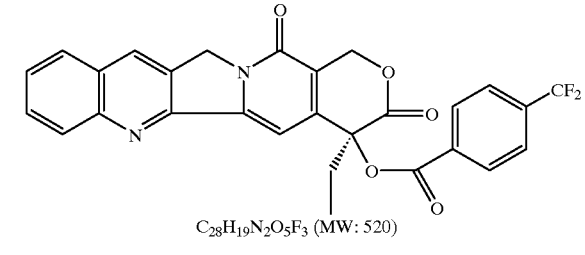
$C_{28}H_{19}N_2O_5F_3$ (MW: 520)
CZ222:
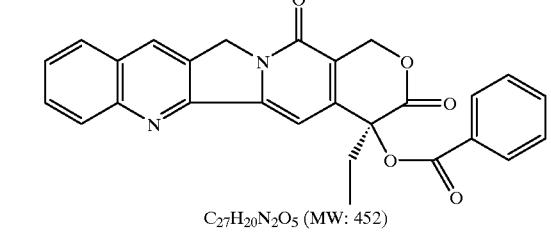
$C_{27}H_{20}N_2O_5$ (MW: 452)

CZ235:

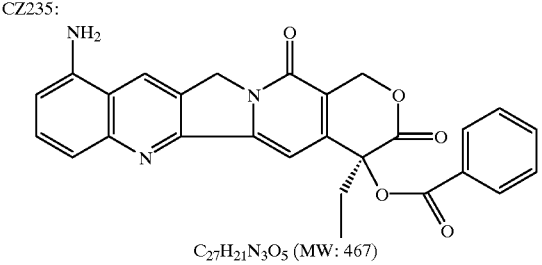

C₂₇H₂₁N₃O₅ (MW: 467)

The preparation is preferably carried out in the following way: The starting camptothecin compound, preferably 2 to 10 molar equivalent of the reacting aromatic acid of the general formula $C_6R_{2-6}COOH$, preferably 2 to 8 molar equivalent of DCC, and a catalytic amount of DMAP are added to about 60–100 ml DMF in a 250 ml round-bottomed flask equipped with a mechanical stirrer. The mixture is stirred at room temperature under nitrogen gas for 72–96 hr. Dicyclohexyl urea formed is removed by filtration. The filtrate is poured onto 500–800 ml ice water while stirring. The crude product is collected by filtration, air-dried at room temperature, then separated by column chromatography with THF-$C_2H_2$ (from 1:7 to 1:15) as eluent. The pure ester prodrug is obtained as white or yellow powders after precipitation from petroleum ether. Reaction yields can range from 5 to 98%.

Any camptothecin compound having an available hydroxyl group may be used to prepare the aromatic esters of the present invention. Suitable camptothecin compounds are described, for example, in U.S. Pat. Nos. 4,894,456, 4,981,968, 5,053,512, 5,049,668, 5,106,742, 5,180,722, 5,244,903, 5,227,380, 5,122,606, 5,122,526, 5,225,404, 4,914,205, 4,545,880, 4,604,463, 4,473,692, 4,031,098, EP 0 220 601, EP 0 074 256. These U.S. and EP patents as well as the earlier mentioned patents and publications are incorporated in their entirety herein by reference for a more complete description of camptothecin compounds which can be employed to prepare the aromatic esters of the present invention as well formulations and methods of using and preparing formulations.

Preferred hydroxyl group containing camptothecin compounds for use in the present invention are carnptothecin itself, 9-nitrocamptothecin and 9-aminocainptothecin. The (R, S,) or (S), versions, or both can be used to prepare the compounds of the present invention. The S-camptothecin is preferred. Accordingly, the aromatic esters of camptothecin can be (R, S,) or (S) aromatic esters of camptothecin.

The compounds disclosed in the present invention were tested against 14 human cell lines and the results are summarized in Table 1 and Table 2. Table 1 shows the average response of 14 human cell lines to camptothecin and its aromatic esters. Table 2 shows the average response of 14 human cell lines to 9-nitrocamptothecin and its aromatic esters. What is interesting from these in vitro data is that the activity of these esters is related to the substituents on their side aromatic rings. The esters with nitro group(s) on their side aromatic ring are more active than the others. Esters without any substitutent on their side aromatic rings such as CZ176 and CZ222 do not show any activity. Thus, the difference in activity among the esters of the present invention are due to the different substituents on their side aromatic ring.

The compounds of the present invention are effective in the treatment of cancer, including, but not limited to, malignant tumors and other forms of cancer. As used herein, the term malignant tumor is intended to encompass all forms of human carcinomas, sarcomas, and melanomas which occurs in the poorly differentiated, moderately differentiated, and well differentiated forms. In administering the compounds of the present invention to patients in need of such treatment, an effective amount of the compound or formulation containing one or more compounds of the present invention is administered to the patient. As used herein, an "effective amount" of the compound of the present invention is intended to mean that amount of the compound which will inhibit the growth of, or retard cancer, or kill cancer or malignant cells, and/or cause the regression and/or palliation of cancer such as malignant tumors, i.e., reduce the volume or size of such tumors or eliminate the tumor entirely.

The compounds of the present invention and formulations of the present invention can be used in the treatment of a number of tumors and/or cancers including, but not limited to, human cancers of the lung, breast, colon, prostate, melanoma, pancreas, stomach, liver, brain, kidney, uterus, cervix, ovaries, urinary track, gastrointestinal, and other solid tumors which grow in a anatomical site other than the blood stream as well as blood borne tumors such as leukemia. Other solid tumors include, but are not limited to, colon and rectal cancer. The compounds of the present invention are also useful as inhibitors of the enzyme topoisomerase I.

The compounds of the present invention can be administered by any acceptable route including, but not limited to, orally, intramuscularly, transdernally, intravenously, through an inhaler or other air borne delivery systems, and the like. Preferably, the compounds and the formulations of the present invention are administered orally, intramuscularly, or transdermally and most preferably delivered orally. Examples of transdermally delivery systems can be found, for instance in U.S. Pat. No. 5,552,154 and 5,652,244 incorporated in their entirety by reference herein. The compounds or formulations of the present invention can also be administered to a patient through a liposome system such as ones described in U.S. Pat. Nos. 5,882,679; 5,834,012; 5,783,211; 5,718,914; 5,631,237; 5,552,156; 5,059,421; 5,000,958; 5,874,105; 5,567,434; 5,549,910; 5,043,165; 5,736,156; 5,567,433; and 4,663,161, all incorporated in their entirety by reference herein.

In addition, the compounds and formulations of the present invention can be used in combination with other drugs and formulations for the treatment of cancers such as taxol, taxotere, or their derivatives as well as cisplatin and derivatives thereof With mammals, including humans, the effective amounts can be administered on the basis of body surface area. The interrelationship of dosages for animals of various sizes, species and humans (based on $mg/M^2$ of body surface) is described by E. J. Freireich et al., Cancer Chemother. Rep., 50(4):219 (1966). Body surface area may be approximately determined from the height and weight of an individual (see, e.g., Scientific Tables, Geigy Pharmaceuticals, Ardsley, N.Y., pp. 537–538 (1970). An effective amount of the camptothecin compounds in the present invention can range from about 12.5 $mg/m^2$ of body surface per day to about 31.3 $mg/M^2$ of body surface per day.

The preferred effective amounts or dosages of the compounds of the present invention in mice are about 1 to about 4 mg per/kg of body weight twice a week for an intramuscular route and about 0.75 to about 1.5 mg per/kg/day for the oral route. Effective amounts or dosages of the compounds of the present invention in mice are, for instance about 1.5 mg/Kg/week to about 10 mg/Kg/week for the transdermal route. For all of the administering routes, the exact timing of administration of the dosages can be varied to achieve optimal results. Generally, when using Intralipid 20 as the carrier for the compound, the actual dosage of the compound reaching the patient may be less. This is due to some loss of the compound on the walls of the syringes, needles, and preparation vessels, which is prevalent with the Intralipid 20 suspension. When a carrier, such as cottonseed oil is used, the above-described loss is not so prevalent because the compound does not adhere as much to the surfaces of syringes, and the like. For instance, and preferably, it has been found that generally about 2.5 mg compound per kg of body weight twice per week using cottonseed oil, administered by an intramuscular route, will deliver the same amount to the patient as 4.0 mg per/kg of body weight twice per week using Intralipid 20 as a carrier. Generally, about 1 mg to about 4 mg of the compound is added to about 0.1 ml to about 1 ml of carrier. Levels of the compounds were well tolerated by mice in the examples set forth below without weight loss or other signs of toxicity. These dosages have been administered for up to six months continuously without any ill effect.

Another important feature of the method provided by the present invention relates to the relatively low or no apparent overall toxicity of the camptothecin compounds administered in accordance herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

The compounds of the present invention may be administered in combination with pharmaceutically acceptable carriers or dilutents, such as Intralipid 10 or 20 or natural oils, or other suitable emulsifiers for lipophilic compounds.

Other features of the present invention will become apparent in view of the following description of exemplary embodiments which are given for illustration of the invention and are not intended to be limiting thereof.

EXAMPLE 1
20-O-phenylcamptothecin

Camptothecin (0.8 g, 0.0023 mol), benzoic acid (1.8 g, 0.014 mol), DCC (1.2 g, 0.0058 mol), and DMAP (0.3 g, 0.0025 mol) were added to 60 ml DMF in a 250 ml round-bottomed flask equipped with a mechanical stirrer. The mixture was stirred under $N_2$ at room temperature for 72 hr. Dicyclohexyl urea formed during the reaction was removed by filtration. The filtrate was poured onto 600 ml ice water while stirring. The stirring was maintained for 30 min. The crude product was collected by filtration. The residue was chromatographically separated with THF-$CH_2Cl_2$ (1:15) as eluent. The pure product (0.4 g) was obtained as white powders by precipitation from petroleum ether. Yield 38%. Mass m/e (relative intensity): 452 ($m^+$, 25), 330 (100), 315 (35), 302 (60), 287 (40), 169 (12), 122 (36), 105 (70), 77 (35), 69 (26); precise mass ($C_{27}H_{20}N_2O_5$): found, 452,137; required, 452.137.

EXAMPLE 2
20-O-p-trifluoromethylphenylcamptothecin

Camptothecin (0.8 g, 0.0023 mol), trifluoro-p-toluic acid (1.6 g, 0.0084 mol), DCC (1.2 g, 0.0058 mol), DMAP (0.3 g, 0.0025 mol) were added to 60 ml DMF all at once. The reaction was done by the same procedure as above. The pure product (1 g) was obtained as white powders, yield 84%. Mass m/e (relative intensity); 520 ($m^+$, 45), 330 (100), 315 (20), 302 (78), 173 (40), 147 (9), 56 (12); precise mass ($C_{28}H_{19}N_2O_5F_3$): found, 520.124; required, 520.125.

EXAMPLE 3
20-O-m-trifluoromethylphenylcamptothecin

With camptothecin (0.8 g, 0.0023 mol), trifluoro-m-toluic acid (1.7 g, 0.0089 mol), DCC (1.2 g, 0.0058 mol), and DMAP (0.3 g, 0.0025 mol) as the starting materials, the pure product (1.07 g) was obtained as white powders by the same procedure as in example 1, yield 89%. Mass m/e (relative intensity): 520 ($m^+$, 50), 330 (100), 315 (40), 302 (97), 287 (38), 246 (6), 190 (10), 173 (56), 145 (38), 124 (3), 75 (3); precise mass ($C_{28}H_{19}N_5F_3$): found, 520.125; required, 520.125.

EXAMPLE 4
20-O-m,p-dinitrophenylcamptothecin

By the same procedure as described in example 1, the pure product (0.13 g) was obtained as white powders with camptothecin (0.8 g, 0.0023 mol), 3, 4-dinitrobenzoic acid (2 g, 0.0094 mol), DCC (1.3 g, 0.0063 mol), and DMAP (0.3 g, 0.0025 mol) as starting materials, yield 10%. Mass m/e (relative intensity): 542 ($m^+$, 10), 330 (100), 315 (38), 302 (78), 287 (42), 272 (12), 195 (10), 168 (40), 120 (20), 75 (18); precise mass ($C_{27}H_{18}N_4O_9$): found, 542.107; required, 542.107.

EXAMPLE 5
20-O-m,m-dinitrophenylcamptothecin

By the same procedure described in example 1, the pure product (1.2 g) was obtained as white powders with camptothecin (0.8 g, 0.0023 mol), 3, 5-dinitrobenzoic acid (2 g, 0.0094 mol), DCC (1.3 g, 0.0063 mol), and DMAP (0.3 g, 0.0025 mol) as starting materials, yield 96%. Mass m/e (relative intensity): 542 ($m^+$, 4), 330 (44), 317 (20), 235 (10), 212 (100), 195 (15), 150 (35), 93 (25), 75 (23); precise mass ($C_{27}H_{18}N_4O_9$): found, 542.109; required, 542.107.

EXAMPLE 6
20-O-p-nitrophenylcamptothecin

By the same procedure described in example 1, the pure product (1.1 g) was obtained as white powders with camptothecin (0.8 g, 0.0023 mol), p-nitrobenzoic acid (2 g, 0.0120 mol), DCC (1.2 g, 0.0063 mol), and DMAP (0.3 g, 0.0025 mol) as starting materials, yield 96%. Mass m/e (relative intensity): 497( $m^+$, 35), 330 (100), 315 (30), 302 (86), 287 (38), 205 (8), 179 (12), 113 (16), 100 (35), 65 (20); precise mass ($C_{27}H_{19}N_3O_7$): found, 497.122, required, 597.122.

EXAMPLE 7
20-O-m-nitrophenylcamptothecin

By the procedure described in example 1, the pure product (1.1 g) was obtained as white powders with camptothecin (0.8 g, 0.0023 mol), m-nitrobenzoic acid (2 g, 0.0120 mol), DCC (1.2 g, 0.0058 mol), and DMAP (0.3 g, 0.0025 mol) as starting materials, yield 96%. $^1$H NMR: δ 1.12 (3H, t, J=7.08 Hz, C19-methyl protons), 2.20–2.60 (2H, m, C18-methylene protons), 5.30 (2H, s, C5-methylene protons), 5.40–5.82 (2H, dd, J=17.53, 17.56 Hz, C17-methylene protons), 7.24 (1H, s, C14-H), 7.56–7.86 (3H, m, C10-H, C11-H, C25-H), 7.88–8.20 (2H, dd, J=8.05, 8.07 Hz, C9-H, C12-H), 8.3–8.55 (3H, m, C24-H, C26-H, C28-H), 8.95 (1H, S, C7-H). $^{13}$C NMR: δ 7.9 (C19), 31.8 (C18), 49.8 (C5), 66.7 (C17), C20 buried in solvent peaks, 95.5 (C14), 120.4, 1224.5, 124.6, 127.7, 127.9, 128.1, 129.5, 129.7, 129.8, 130.1, 130.5, 130.9, 135.7, 145.0, 146.4, 148.1, 148.5, 151.9, 159.0 (C2, C3, C6–C13, C15, C16, C16a, C23–C28), 163.0, 166.9 (C21, C22). Mass m/e (relative intensity): 497 ($m^+$, 6), 330 (28), 315 (12), 302 (18), 287 (15), 167 (100), 121 (40), 100 (10), 65 (35); precise mass ($C_{27}H_{19}N_3O_7$): found, 497.122; required 497.122.

EXAMPLE 8
20-O-phenyl-9-nitrocamptothecin

By using the procedure described in example 1, the pure product (0.2 g) was obtained as yellow powders with 9-nitrocamptothecin (1.5 g, 0.0038 mol), benzoic acid (1 g, 0.0082 mol), DCC (1.7 g, 0.0083 mol), and DMAP (0.3 g, 0.0025 mol) as starting materials, yield 11%. Mass m/e (relative intensity): 497 ($m^+$, 10), 392 (6), 375 (100), 360 (35), 347 (80), 332 (30), 319 (15), 302 (10), 286 (20), 274 (8), 258 (5), 216 (7); precise mass ($C_{27}H_{19}N_3O_7$): found, 497.123; required, 497.122.

EXAMPLE 9
20-O-m-nitrophenyl-9-nitrocamptothecin

By using the same procedure as described in example 1, the pure product (0.3 g) was obtained as yellow powders with 9-nitrocamptothecin (0.6 g, 0.0015 mol), 3-nitrobenzoic acid (0.8 g, 0.0048 mol), DCC (1 g, 0.0049 mol), and DMAP (0.2 g, 0.0016 mol) as starting materials, yield 37%. $^1$H NMR: δ 1.13 (3H, t, J=7.0 Hz, C19-methyl protons), 2.30–2.60 (2H, m, C18-methyl protons), 5.40 (2H, S, C5-methylene protons),5.46–5.85 (2H, dd, J=17.50, 17.55 Hz, C17-methylene protons), 7.25 (1H, S, C14-H), 7.72 (1H, t, J=8.02 Hz, C25-H), 7.88 (1H, t, J=8.01 Hz, C11-H), 8.37–8.52 (4H, m, C10-H, C12-H, C24-H, C26-H), 8.95 (1H, S, C28-H), 9.28 (1H, S, C7-H); $^{13}$C NMR: δ 7.9 (C19), 32.0 (C18), 50.8 (C5), 67.5 (C17), C20 buried by $CHCl_3$ peaks, 96.7 (C14), 121.0, 121.8, 125.0, 126.1, 127.7, 128.5, 128,8, 130.1, 130.8, 131.6, 135.9, 136.5, 145.5, 146.0, 148.2, 148.5, 157.0, (C2, C3, C6–C13, C15, C16, C16a, C23–C28), 163.4, 166.9 (C21,C22). Mass m/e (relative intensity): 542 ($m^+$, 3), 389 (20), 375 (100), 360 (38), 347 (78, 332 (58), 306 (30), 286 (261), 272 (15), 258 (15), 258 (10), 229(8); precise mass ($C_{27}H_{18}N_4O_9$): found 542.107; required 542.107.

EXAMPLE 10
20-O-o-fluorophenyl-9-nitrocamptothecin

With 9-nitrocamptothecin (0.5 g, 0.0013 mol), 2-fluorobenzoic acid (1 g, 0.0071 mol), DCC (1.5 g, 0.0073 mol, and DMAP (0.2 g, 0.0016 mol) were used as starting reaction materials, the pure product (0.12 g) was obtained as yellow powders, yield 18%. $^1$H NMR: δ 1.12 (3H, t, J=7.08 Hz, C19-methyl protons), 2.20–2.50 (2H, m, C18-methylene protons,), 5.39 (2H, S, C5-methylene protons), 5.45–5.84 (2H, dd, J=17.51, 17.58 Hz, C17-methylene protons), 7.24 (1H, S, C14-H), 7.16–7.40 (2H, m, C24-H, C27-H), 7.52–7.70 (1H, m, C25-H), 7.09 Hz, C11-H), 8.05 (1H, t, J=6.8 HZ, C26-H), 8.36–8.60 (2H, m, C10-H, C12-H), 9.28 (1H, S, C7-H); $^{13}$C NMR: δ 7.9 (C19), 3.20 (C18), 50.6 (C5), 67.4 (C17), C20 buried by $CHCl_3$ peaks, 97.1 (C14), 117.0, 117.6, 112.0, 121.6, 124.4, 125.9, 127.4, 128.7, 131.4, 122.8, 135.8, 136.7, 145.0, 146.6, 157.2, 160.8 (C2, C3, C6–C13, C15, C16, C16a, C23–C28), 164.5, 167.2 (C22, C22). Mass m/e (relative intensity): 515 ($m^+$, 2), 375 (22), 347 (18), 332 (8), 286(3), 140 (63), 123 (100), 45 (36), 75 (16); precise mass ($C_{27}H_{18}N_3O_7F$); found, 515.113; required, 515.113.

EXAMPLE 11
20-O-o-fluorophenyl-9-nitrocamptothecin

With 9-nitrocamptothecin (0.5 g, 0.0013 mol), 3-fluorobenzoic acid (1 g, 0.0071 mol), DCC (1.5 g, 0.0073 mol), and DMAP (0.2 g, 0.0016 mol) as starting materials, the pure product (0.6 g) was obtained as yellow powders, yield 90%. $^1$H NMR: δ 1.12 (3H, t, J=7.08 Hz, C19-methyl protons), 2.23–2.55 (2H, m, C18-methyl protons), 5.33 (2H, S, C5-methylene protons), 5.42–5.82 (2H, dd, J=17.50, 17.54 Hz, C 17-methylene protons), 5.42–5.82 (2H, dd, J=17.50, 17.541 Hz, C17-methylene protons), 7.25 (1H, S, C14-H), 7.30–7.52 (2H, m, C24-H, C26-H), 7.75–7.93 (3H, m, C14-H, C25-H, C28-4), 8.40–8.50 (2H, d, J=8.08 Hz, C10-H, C12-H), 9.25 (1H, S, C7-H); $^{13}$C NMR: 87.9 (C19), 32.0 (C18), 50.8 (C5), 67.5 (C17), C20 buried by solvent peaks, 97.0 (C14), 118.0, 118.2, 121.0, 121.4, 122.0, 126.2, 127.4, 128.6, 131.0, 131.2, 131.9, 137.0, 145.0, 145.5, 145.7, 148.5, 153.9, 157.5, 161.0 (C2, C3, C6–C13, C15, C16, C16a, C23–C28), 164.3, 167.0, (C21, C22). Mass m/e (relative intensity): 515 ($m^+$, 7), 375 (38), 347 (32), 332 (10), 286 (3), 140(60), 123(100), 95 (50), 175 (15); precise mass ($C_{27}H_{18}N_3O_7F$): found, 515.133, required, 515.133.

EXAMPLE 12
20-O-p-cyanophenyl-9-nitrocamptothecin

With 9-nitrocamptothecin (0.58 g, 0.0015 mol), 4-cyanobenzoic acid (1 g, 0.0068 mol), DCC (1.5 g, 0.0073 mol), and DMAP (0.2g, 0.0016 mol) as starting materials, the pure product (0.3 g) was obtained as yellow powders, yield 38%. $^1$H NMR: δ 1.15 (3H, t, J=7.05 Hz, C19-methyl protons), 2.30–2.60 (2H, m, C18-methylene protons), 5.44 (2H, S, C14-H), 5.55–5.85 (2H, dd, J=17,50, 17.53 Hz, C17-methylene protons), 7.30 (1H, S, C14-H), 7.85 (2H, d, J=8.08 Hz, C24-H, C28-H, 7.94 (1H, t, J=8.02 Hz, C11-H), 8.26 (2H, d, J=8.09 Hz, C25-H, C27-H), 8.45–8.55 (2H, m, C10-H, C12-H), 9.33 (1H, s, C7-H); $^{13}$C NMR: δ 8.0 (C19),32.0 (C18),50.6 (C5), 67.5 (C17), C20 buried by solvent peaks in the area of 76.0–78.0 ppm,96.6(C14), 117.2, 117.3, 121.0, 121.4, 126.0, 127.5, 128.5, 130.6, 131.6, 132.7, 136.7, 145.2, 145.9, 149.0, 153.9, 157.4, (C2, C3, C6–C13, C15, C16, C16a, C23–C28, C26-cyano carbon), 163.6, 166.8 (C21, C22). Mass m/e (relative intensity): 522(m+,2), 389 (4), 375 (100), 360 (35), 347 (85), 332 (55), 306 (20), 286 (25), 272 (8), 229(5), 203 (2); precise mass ($C_{28}H_{18}N_4O_7$): found, 522.118; required 522.118.

EXAMPLE 13
20-O-m-cyanophenyl-9-nitrocamptothecin

With 9-nitrocamptothecin (0.5 g, 0.0013 mol), 3-cyanobenzoic acid (1 g, 0.0068 mol), DCC (1.5 g, 0.0073 mol), and DMAP (0.2 g, 0.0016 mol) as starting materials, the pure product (0.26 g) was obtained as yellow powders, yield 38%. $^1$H NMR: δ 1.14 (3H, bs, C19-methyl protons), 2.25–2.26 (2H, m, C18-methylene protons), 5.38 (2H, s, C5-methylene protons), 5.40–5.78 (2H, dd J=17.50, 17.54 Hz, C17-methylene protons), 7.21 (1H, s, C14-H), 7.60–7.70 (1H, m, C25-H), 7.80–7.96 (2H, m, C11-H, C24-H), 8.25–8.55 (4H, m, C10-H, C12-H, C26-H, C28-H), 9.28 (1H, s, C7-H); $^{13}$C NMR: 7.9 (C19), 32.5 (C18), 50.8 (C5), 67.5 (C17), C20 buried by $CHCl_3$ peaks in the area of 7.60–178.0 ppm, 96.8 (C14), 113.2, 117.8, 121.0, 121.8, 126.1, 127.8, 128.8, 129.9, 130.1, 131.6, 133.9, 134.1, 136.7, 137.0, 145.4, 146.0, 148.4, 153.1, 156.1, 156.5 (C2, C3, C6–C13, C15, C216, C16a, C23–C28, C27-cyano carbon), 163.1, 166.5 (C21, C22). Mass m/e (relative intensity): 522 ($m^+$, 3), 389 (18), 375 (100), 360 (40), 347 (80), 332 (61), 306 (56), 286 (35), 272(15), 216 (10); mass ($C_{28}H_{18}N_4O_7$): found, 522.117; required, 522.118.

EXAMPLE 14
20-O-p-fluorophenyl-9-nitrocamptothecin

With 9-nitrocamptothecin (0.5 g, 0.0013 mol), 4-fluorobenzoic acid (1 g, 0.0071 mol), DCC (1.5 g, 0.0073 mol), and DMAP (0.2 g, 0.0016 mol) as starting materials, the pure product (0.15 g) was obtained as yellow powders, yield 22%. $^1$H NMR: δ 1.10 (3H, t, J=7.04 Hz, C19-methyl protons), 2.20–2.50 (2H, m, C18-methylene protons), 5.38 (2H, S, C5-methylene protons), 5.41–5.82 (2H, dd, J=17.42, 17.49 Hz, C17-methylene protons), 7.18 (2H, t (d+d), J=8.05 Hz, C25-H,C27-H), 7.27 (1H, S, C14-H), 7.85 (1H, t, J=8.04 Hz, C11-H), 8.10–8.20 (2H, d+d, J=8.06, 8.05 Hz, C24-H, C28-H), 8.45 (2H, d, J=8,08 Hz, C10-H, C12-H), 9.26 (1H, s, C7-H); $^{13}$C NMR: δ 7.9 (C19), 32.2 (C18), 50.6 (C5), 67.6 (C17), C20 buried by solvent peaks in the area of 76.0–78.0 ppm, 97.3 (C14), 116.0, 116.3, 121.0, 121.6, 125.0, 126,0, 127.5, 128., 131.6, 133.2, 136.3, 145.0, 146.0, 148,6, 153.4, 156.8, 157.0 (C2, C3, C6–C13, C15, C16, C16a, C23–C28), 164.2, 168,1 (C21,C22). Mass m/e(relative intensity): 515 (m$^+$, 8), 375 (60), 360 (14), 347 (50), 332 (10), 155 (6), 140 (18), 123 (100), 95(30); precise mass ($C_{27}H_{18}N_3O_7F$): found, 515.113; required, 515.113.

EXAMPLE 15
20-O-0-chlorophenyl-9-nitrocamptothecin

With 9-nitrocamptothecin (0.5 g, 0.0013 mol), 2-chlorobenzoic acid (1 g, 0.0063 mol), DCC (1.5 g, 0.0073 mol), and AMAP (0.2 g, 0.0016 mol) as starting materials, the pure product (0.25 g) was obtained as yellow powders, yield 36%. $^1$H NMR: δ 1.12 (3H, t, J=7.10 Hz, C19-methyl protons), 2.20–2.50 (2H, m, C18-methylene protons), 5.38 (2H, s, C5-methlene protons), 5.42–5.85 (2H, dd, J=17.51, 17.56 Hz, C17-methylene protons), 7.38 (1H, s, C14-H), 7.35–7.50 (3H, m, C14–H,H,C26-H,C27-H), 7.87 (1H, t, J=8.08 Hz, C11-H), 8.05 (1H, d, J=8.06 Hz, C24-H), 8.44–8.54 (2H, d+d, J=8.05, 8.08 Hz, C10-H, C12-H), 9.26 (1H, s, C7-H); $^{13}$C NMR: δ 7.9 (C19), 32.3 (C18), 50.8(C5), 67.7 (C17), C20 buried by solvent peaks in the area of 76.0–78.0 ppm, 97.3 (C14), 121.0, 121.2, 125.9, 126.9, 127.4, 128.7, 131.3, 131.6, 132.2, 133.7, 134.8, 136.8, 145.0, 146.0, 148.8, 153.7, 156.6, 158.9 (C2, C3, C6–C13, C15, C16, C16a, C23–C28), 164.0, 166.8 (C21,C22). Mass m/e(relative intensity): 531(m$^+$, weak), 375 (100), 360 (20), 347 (85), 335 (80), 285 (38), 235 (38), 185 (8), 147 (75), 139 (85), 111 (18), 97 (25), 77 (15); precise mass ($C_{27}H_{18}N_3O_7Cl$): found, 531.083; required, 531.083.

EXAMPLE 16
20-O-p-chlorophenyl-9-nitrocamptothecin

With 9-nitrocamptothecin (0.5 g, 0.0013 mol), 4-chlorobenzoic acid (0.5 g, 0.0032 mol), DCC (1 g, 0.0049 mol), and DMAP (0.2 g, 0.0016 mol) as starting materials, the pure product (0.05 g) was obtained as yellow powders, yield 7%. $^1$H NMR: δ 1.11 (3H, t, J=7.06 Hz, C19-methyl protons), 2.20–2.50 (2H, m, C18-methylene protons), 5.35 (2H, s, C5-methylene protons), 5.40–5.82 (2H, dd, J=17.51, 17.55 Hz, C17-methylene protons), 7.23 (1H, S, C14-H), 7.47 (2H, d, J=8.09 Hz, C25-H, C27-H), 7.86 (1H, t, J=8.0 Hz, C11-H), 8.04 (2H, d, J=8.07 Hz, C24-H, C28-H), 8.43 (2H, d, J=8.03 Hz, C10-H, C12-H), 9.25 (1H, s, C7-H); $^{13}$C NMR: δ 7.9 (C19), 50.5 (C5), 67.2 (C17), C20 buried by solvent peaks in the area of 76.0–78.0 ppm, 96.8 (C14), 120.9, 121.5, 125.9, 127.4, 128.8, 129.1, 131.5, 136.5, 140.4, 145.0, 145.8, 145.9, 148.7, 153.6, 157.0 (C2, C3, C6–C13, C15, C16, C16a, C23–C28), 164.5, 167.0 (C21, C22). Mass m/e (relative intensity): 531 (m$^+$, weak), 375 (95), 360 (35), 347 (70), 332 (38), 156 (43), 139 (100), 111 (35), (10); precise mass ($C_{27}H_{18}N_3O_7Cl$): found, 531.083, required, 531.083.

EXAMPLE 17
20-O-m-chlorophenyl-9-nitrocamptothcin

With 9-nitrocamptothecin (0.5 g, 0.0013 mol), 3-chlorobenzoic acid (0.5 g, 0.0032 mol), DCC (0.8 g, 0.0039 mol), and DMAP (0.2 g, 0.0016 mol) as starting materials, the pure product (0.06 g) was obtained as yellow powders, yield 9%. $^1$H NMR: δ 61.10 (3H, t, J=7.04 Hz, C19-methyl protons), 2.20–2.54 (2H, m, C18-methyl protons), 5.38 (2H, s, C5-methylene protons), 5.40–5.83 (2H, dd, J=17.52, 17.55 Hz, C17-methylene protons), 7.23 (1H, s, C14-H), 7.44 (1H, t (d+d), J=8.06 Hz, C25-H), 7.59 (1H, d, J=8.08 Hz, C26-H), 7.86 (1H, t (d+d), J=8.08 Hz, C11-H), 7.98 (1H, d, J=8.04 Hz, C24-H), 8.10 (1H, s, C28-H), 8.45 (2H, d, J=8.06 Hz, C10-H, C12-H), 9.25 (1H, s, C7-H); $^{13}$C NMR: δ 7.9 (C19), 32.0 (48), 50.4 (C5), 67.0 (C17), C20 buried by solvent peaks in the area of 76.0–78.0 ppm, 96.9 (C14), 120.8, 121.5, 125.8, 127.4, 128.3, 128.6, 129.7, 129.8, 129.9, 131.2, 134.0, 134.9, 136.6, 144.9, 145.5, 145.8, 148.8, 157.2 (C2, C3, C6–C13, C15, C16, C16a, C23–C28), 164.2, 167.1 (C21, C22). Mass m/e (relative intensity): 531 (m$^+$, 1), 375 (35), 360 (6), 347 (25), 243 (15), 231 (15), 156 (100), 139 (90), 119 (82), 111 (35), 100 (28), 75 (8); precise mass ($C_{27}H_{18}N_3O7Cl$): found, 531.084; required 531.083.

EXAMPLE 18
20-O-p-nitrophenyl-9-nitrocamptothecin

With 9-nitrocamptothecin (0.5 g, 0.0013 mol), 4-nitrobenzoic acid (0.5 g, 0.0030 mol), DCC (0.8 g, 0.0039 mol), and DMAP (0.2 g, 0.0016 mol) as starting materials, the pure product (0.18 g) was obtained as yellow powders, yield 26%. $^1$H NMR: δ 1.11 (3H, t, J=7.05 Hz, C19-methyl protons), 2.20–2.53 (2H, m, C18-methylene protons), 5.39 (2H, s, C5-methylene-protons), 5.40–5.83 (2H, dd, J=17.50, 17.54 Hz, C17-methylene protons), 7.22 (1H, s, C14-H), 7.86 (1H, t (d+d), J=8.03 Hz, C11-H), 8.20–8.60 (6H, m, C10-H, C12-H, C24-H, C25-H,C27-H, and C28-H), 9.25 (1H, s, C7-H); $^{13}$C NMR: δ 7.9 (C19), 32.1 (C5), 67.3 (C17), C20 buried by solvent peaks in the area of 76.0–78.0 ppm,96.6 (C14), 121.0, 121.8, 123.9, 126.0, 127.8, 128.8, 130.3, 131.4, 131.5, 133.9, 136.5, 137.0, 145.1, 146.0, 148.5, 151.4, 153.5, 157.0 (C2, C3, C6–C13, C15, C16, C16a, C23–C28), 163.6, 166.6 (C21, C22). Mass m/e (relative intensity): 542(m$^+$, 8), 375 (95), 347 (100), 333 (14), 304 (8), 258 (6), 203(4); Precise mass ($C_{27}H_{18}N_4O_9$): found, 542.109; required, 542.107.

EXAMPLE 19
20-O-o-nitrophenyl-9-nitrocamptothecin

With 9-nitrocamptothecin (0.8 g, 0.0020 mol), 2-nitrobenzoic acid (0.8 g, 0.0048 mol), DCC (1 g, 0.0049 mol), and DMAP (0.2 g, 0.0016 mol) as starting materials, two isomers were obtained as yellow powders, total yield 9%.

Isomer 1 has a structure as shown below:

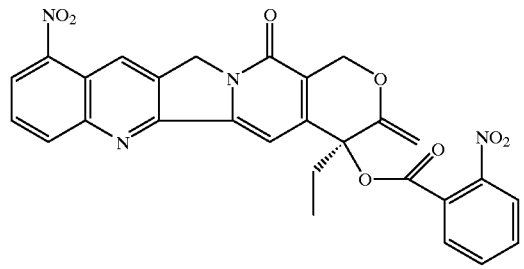

$^1$H NMR: δ 1.05 (3H, t, J=7.08 Hz, C19-methyl protons), 2.25–2.42 (2H, m, C18-methylene protons), 5.44 (2H, s, C5-methylene protons), 5.45–5.82 (2H, dd, J=17.51, 17.58 Hz, C17-methylene protons), 7.24 (1H, s, C14-H), 7.60–8.58 (7H, m, C10-H, C11-H, C12-H, C24-H, C26-H, and C27-H), 9.26 (1H, s, C7-H); $^{13}$CNMR: δ 7.9 (C19), 32.0 (C18), 50.8 (C5), 67.5 (C17), 78.0 (C20), 97.9 (C14), 121.1, 124.1, 126.0, 127.4, 128.7, 131.0, 131.4, 132.7, 133.5, 137.1, 145.5, 145.8, 149.0, 154.0, 157.5 (C2, C3, C6–C13, C15, C16, C16a, C23–C28), 164.0, 167.0 (C21, C22). Mass m/e (relative intensity): 542 (m$^+$, 2), 389 (38), 375 (85), 347 (100), 361 (35), (80), 306 (55), 286 (36), 272 (25), 260 (16), 230 (18), 203 (12); precise mass ($C_{27}H_{18}N_4O_9$): found, 542.108; required, 542.107.

Isomer 2 has a structure as shown below:

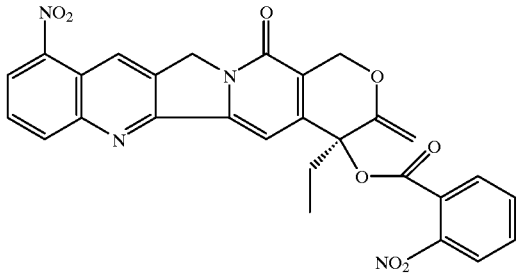

$^1$H NMR: δ 1.14 (3H, t, J=7.06 Hz, C19-methyl protons), 2.28–2.46 (2H, m, C18-methylene protons), 5.40 (2H, s, C5-methylene protons), 5.45–5.84 (2H, dd, J=17.50, 17.55 Hz, C17-methylene protons), 7.25 (1H, s, C14-H), 7.60–8.58 (7H, m, C10-H, C11-H, C12-H, C25-H,C26-H, C27-H, and C28-H), 9.35 (1H, s, C7-4); $^{13}$C NMR: δ 7.9 (C19), 32.1 (C18), 50.8 (C5), 67.5 (C17), 78.0 (C20), 96.6 (C14), 121.4, 124.0, 126.0, 127.5, 128.8, 131.1, 131.4, 132.7, 133.3, 137.1, 145.4, 145.8, 148.9, 149.2, 157.6 (C2, C3, C6–C13, C15, C16, C16a, C23–C28), 164.0, 167.0 (C21,C22). Mass m/e (relative intensity): 542(m$^+$, 2), 389 (38), 375 (85), 347 (100), 361(35), 332 (80), 306 (55), 286 (36), 272 (25), 260 (16), 230 (18), 203 (12); precise mass ($C_{27}H_{18}N_4O_9$): found, 542.108; required 542.107.

EXAMPLE 20
20-O-o-hydroxylphenyl-9-nitrocamptothecin

With 9-nitrocamptothecin (0.5 g, 0.0013 mol), 2-hydroxylbenzoic acid (0.5 g, 0.0036 mol), DCC (0.75 g, 0.0036 mol), and DMAP (0.2 g, 0.0016 mol) as starting materials, the pure product (0.03 g) was obtained as yellow powders, yield 5%. $^1$H NMR: δ 1.11 (3H, t, J=7.05 Hz, C19-Methyl protons), 2.20–2.52 (2H, m, C18-methylene protons), 5.40 (2H, s, C5-methylene protons), 5.41–5.85 (2H, dd, J=17.51, 17.55 Hz, C17-methylene protons), 6.80–7.06 (2H, m, C25-H, C27-H), 7.24 (1H, s, C14-H), 7.55 (1H, t (d+d), J=8.02 Hz, C26-H), 7.90 (1H, t (d+d), J=8.05 Hz, C11-H), 8.10 (1H, d, J=8.03 Hz, C24-H), 8.45 (2H, d, J=8.04 Hz, C10-H, C12-H), 9.25 (1H, s, C7-H), 10.0 (1H, s, C28-phinolic proton); $^{13}$C NMR: δ 7.9 (C19), 32.0 (C18), 50.3 (C5), 67.5 (C17), C20 buried by solvent peaks in the area of 76.0–78.0 ppm, 96.9 (C14), 111.0, 118.1, 119.7, 121.0, 121.6, 126.0, 127.5, 128.8, 130.2, 131.3, 137.0, 137.2, 145.0, 145.2, 145.5, 148.5, 153.5, 157.3 (C2, C3, C6–C13, C15, C16, C16a, C23–C28), 162.5, 168.6 (C21, C22). Mass m/e (relative intensity): 513 (m$^+$, 1), 375 (25), 347 (12), 138 (62), 120 (100), 92 (56), 64 (10); precise mass ($C_{27}H_{19}N_3O_8$): found, 513.116; required, 513.117.

EXAMPLE 21
20-O-m-bromophenyl-9-nitrcamptothecin

With 9-nitrocarnptothecin (0.5 g, 0.0013 mol), 3-bromobenzoic zcid (0.5 g, 0.0025 mol), DCC (0.75 g, 0.0036 mol), and DMAP (0.2 g, 0.0016 mol) as starting materials, the pure product (0.06 g) was obtained as yellow powders, yield 8%. $^1$H NMR: δ 1.10 (3H, t, J=7.04 Hz, C19-methyl protons), 2.20–2.52 (2H, m, C18-methylene protons), 5.40 (2H, s, C5-methylene protons), 5.41–5.85 (2H, dd, J=17.50, 17.55 Hz, C17-methytlene protons), 7.24 (1H, s, C14-H), 7.36 (1H, t, J=8.03 Hz, C25-H), 7.76 (1H, d, J=8.04 Hz, C26-H), 7.88 (1H, t, J=8.05 Hz, C11-H), 8.05 (1H, d, J=8.06 Hz, C24-H), 8.26 (1H, s, C28-H), 8.48 (2H, d, J=8,05 Hz, C10-H, C12-H), 9.25 (1H, s, C7-H); $^{13}$C NMR: δ 7.9 (C19), 50.4 (C5), 67.5 (C17), C20 buried by CHCl$_3$, 96.9 (C14), 121.0, 121.8, 122.5, 125.9, 127.6, 128.7, 128.9, 130.2, 130.5, 131.3, 133.1, 136.6, 137.0, 145.1, 145.7, 145.9, 148.5, 153.5, 157.0, 157.6 (C2, C3, C6–C13, C15, C16, C16a, C23–C28), 164.0, 167.0 (C21, C22). Mass m/e (relative intensity): 575 (m$^+$, 5), 389 (10), 375 (100), 360 (35), 347 (74), 332 (48), 318 (8), 296 (16), 258 (8), 224 (8); precise mass ($C_{27}H_{18}N_3O_7Br$): found, 575.032; required, 575.034.

EXAMPLE 22
20-O-o-bromophenyl-9-nitrocamptothecin

With 9-nitrocamptothecin (0.5 g, 0.0013 mol), 2-bromobenzoic acid (1 g, 0.0050 mol), DCC 90.75 g, 0.0036 mol), and DMAP (0.2 g, 0.0016 mol) as starting materials, the pure product (0.14 g) was obtained as yellow powders, yield 19%. Mass m/e (relative intensity): 577 (M+2, 5), 575 (m$^+$, 5), 375 (58), 347 (38), 332 (12), 286 (4), 202(26), 183(36), 84 (100); precise mass ($C_{27}H_{18}N_3O_7Br$): found, 575.032; required 575.033.

EXAMPLE 23
20-O-o,p-dinitrophenyl-9-nitrocamptothecin

With 9-nitrocamptothecin (0.8 g, 0.0020 mol), 2,4-dinitrobenzoic acid (2 g, 0.0094 mol), DCC (1 g, 0.0049 mol), and DMAP (0.2 g, 0.0016 mol) as starting materials, the pure product (0.1 g) was obtained as yellow powders, yield 9%. $^1$H NMR: δ 1.08 (3H, t, J=7.56 Hz, C19-methyl protons), 2.15–2.40 (2H, m, C-18-methylene protons), 5.40 (2H, s, C5-methylene protons), 5.41–5.85 (2H, dd, J=17.50, 17.58 Hz, C17-methylene protons), 7.58 (1H, s, C14-H), 7.94 (1H, t, J=8.08 Hz, C11-H), 8.15 (1H, d, J=8.06 Hz, C10-H), 8.45–8.70 (3H, m, C12-H, C27-H, C28-H), 8.86 (1H,s, C24-H), 9.28 (1H, s, C7-H); $^{13}$C NMR: δ 7.9 (C19), 31.6 (C18), 51.0 (C5), 6.75 (C17), 79.0 (C20), 97.5 (C14)), 119.8, 121.4, 126.0, 127.4, 128.0, 128.6, 131.6, 131.8, 132.2, 137.0, 145.5, 145.8, 146.0, 147.5, 149.2, 149.4, 153.5, 157.4 (C2, C3, C6–C13, C15, C16, C16a, C23–C28), 164.0, 167.8 (C21, C22). Mass m/e (relative intensity): 587(m$^+$, weak), 389 (4), 377 (6), 347 (6), 306 (5), 212 (75), 168 (100), 120 (85), 75 (70); precise mass ($C_{27}H_{18}N_5O_{11}$): found, 587.092; required, 587.092.

EXAMPLE 24
20-O-m,m-dinitrophenyl-9-nitrocamptothecin

With 9-nitrocamptothecin (0.8 g, 0.0020 mol), 3,5-dinitrobenzoic acid (1.5 g, 0.0071 mol), DCC (1.3 g, 0.0063 mol), and DMAP (0.3 g, 0.0025 mol) as starting materials, the pure product (0.9 g) was obtained as yellow powders, yield 77%. $^1$H NMR: δ 1.10 (3H, t, J=7.50 Hz, C19-methyl protons), 2.30–2.60 (2H, m, C18-methylene protons), 5.37 (2H, s, C2-methylene protons), 5.40–5.84 (2H, dd, J=17.50, 17.55 Hz, C17-methylene protons), 7.20 (1H, s, C14-H), 7.88 (1H, t, J=8.15 Hz, C11-H), 8.35–8.50 (2H, t (dd), J=8.09 Hz, C10-H, C12-H), 9.18 (2H, strong s, C24-H, C28-H), 9.30 (2H, s, C7-H, C26-H); $^{13}$CNMR: δ 17.8 (C19), 32.0 (C18), 50.6 (C5), 67.6 (C17), 78.8 (C20), 96.5 (C14), 121.0, 122.1, 123.5, 126.4, 128.0, 129.1, 130.0, 131.6, 132.3, 136.4, 144.5, 145.1, 145.8, 149.0, 153.2, 157.4 (C2, C3, C6–C13, C15–C16, C16a, C23–C28), 161.5, 166.4

(C21, C22). Mass m/e (relative intensity): 587(m+, weak), 389 (1), 377 (3), 306 (2), 212 (100), 166 (26), 120 (20), 75(40); precise mass ($C_{27}H_{17}N_5O_{11}$): found, 587.092; required, 587.092.

EXAMPLE 25
20-O-p-trifluoromethylphenyl-9-nitrocamptothecin

With 9-nitrocamptothecin (0.5 g, 0.0013 mol), 4-trifluoromethylbenzoic acid (1 g, 0.0053 mol), DCC (0.8 g, 0.0039 mol), and DMAP (0.2 g, 0.0016 mol) as starting materials, the pure product (0.35 g) was obtained as yellow powders, yield 48%. $^1$H NMR: δ 1.10 (3H, t, J=7.05 Hz, C19-methyl protons), 2.20–2.52 (2H, m, C18-methylene protons), 5.39 (2H, s, C5-methylene protons), 5.40–5.82 (2H, dd, J=17.50, 17.55 Hz, C17-methylene protons), 7.22 (1H, s, C14-H), 7.78 (2H, d, J=8.03 Hz, C25-H, C27-H), 7.86 (1H, t, J=8.04 Hz, C11-H), 8.24 (2H, d, J=8,06 Hz, C24-H, C28-H), 8.45 (2H, d, J=8,06 Hz, C10-H, C12-H), 9.25 (1H, s, C7-H); $^{13}$C NMR: δ 7.9 (C19), 32.0 (C18), 50.4 (C5), 67.5 (C17), C20 buried by $CHCl_3$ peaks, 96.8 (C14), 121.0, 121.6, 125.8, 126.0, 127.5, 128.7, 130.6, 131.5, 131.9, 136.5, 145.0,145.2, 145.8, 148.5, 153.5, 157.0 (C2, C3, C6–C13, C15, C16a, C23–C28), 164.7, 166.8 (C21, C22). Mass m/e (relative intensity): 565(m+, 4), 375 (50), 360 (20), 347 (48), 332 (15), 302 (6), 190 (45), 173 (100), 145 (60), 95 (45); precise mass ($C_{28}H_{18}N_3O_7F_3$): found, 565.109; required, 565.110.

EXAMPLE 26
20-O-m-trifluoromethylphenyl-9-nitrocamptothecin

With 9-nitrocamptothecin (0.5 g, 0/0013 mol), 3-trifluoromethylbenzoic acid (1 g, 0.0053 mol), DCC (0.8 g, 0.0039 mol), and DMAP (0.2 g, 0.0016 mol) as starting materials, the pure product (0.45 g) was obtained as yellow powders, yield 61%. $^1$H NMR: δ 1.10 (3H, t, J=7.08 Hz, C19-methyl protons), 2.20–2.50 (2H, m, C18-methylene protons), 5.38 (2H, s, C5-methylene protons), 5.40–5.85 (2H, dd, J=17.51, 17.58 Hz, C17-methyl protons), 7.24 (1H, s, C14-H), 7.65 (1H, t, J=8.08 Hz, C25-H), 7.82–7.95 (2H, m, C11-H, C26-H), 8.28 (1H, d, J=8.07 Hz, C24-H), 8.38 (1H, s, C28-H), 8.47 (2H, d, J=8.06 Hz, C10-H, C12-H), 9.25 (1H, s, C7-H); $^{13}$C NMR: δ 7.9 (C19), 32.0 (C18), 50.5 (C5), 67.6 (C17), 76.2 (C27-trifluoromethyl carbon), 77.2 (C20), 96.9 (C14), 121.0, 121.4, 126.0, 127.2, 127.5, 128.7, 129.4, 129.8, 130.7, 131.4, 133.3, 136.4, 145.2, 145.3, 148.8, 153.5, 157.0 (C2, C3, C6–C13, C15, C16, C16a, C23–C28), 164.0, 167.1 (C21, C22). Mass m/e (relative intensity): 565 (m+, 3), 375 (18), 360 (5), 34 (18), 332 (4), 190 (68), 173 (100), 145 (85), 95 (8); precise mass (C28H18N3O7F3): found, 565.110; required, 565.110.

EXAMPLE 27
20-O-p-methyl-m,m-dinitrophenyl-9-nitrocamptothecin

With 9-nitrocamptothecin (0.8 g, 0.0020 mol), 4-methyl3, 5-dinitrobenzoic acid (2 g, 0.0088 mol), DCC (1.3 g, 0.0063 mol), and DMAP (0.3 g, 0.0025 mol) as starting materials, the pure product (0.15 g) was obtained as yellow powders, yield 12%. $^1$H NMR: δ 1.12 (3H, t, J=7.08 Hz, C19-methyl protons), 2.20–2.60 (2H, m, C18-methylene protons), 2.68 (3H, s, C26-methyl protons), 5.40 (2H, s, C5-methylene protons), 5.41–5.84 (2H, dd, J=17.52, 17.56 Hz, C17-methylene protons), 7.20 (1H, s, C14-H), 7.90 (1H, t, J=8.08 Hz, C11-H), 8.45 (2H, d, J=8.06 Hz, C10-H, C12-H), 8.64 (2H, s, C24-H, C28-H), 9.27 (1H, s, C7-H); $^{13}$C NMR: δ 7.9 (C19), 15.0 (C26-methyl carbon), 32.4 (C18), 50.5 (C5), 67.4 (C17), 78.0 (C20), 96.8 (C14), 121.0, 121.8, 125.4, 126.0, 127.6, 128.2, 128.3, 129.0, 129.2, 131.5, 132.8, 136.6, 144.5, 145.9, 146.1, 148.9, 152.1, 153.6, 157.2 (C2, C3, C6–C13, C15, C16, C16a, C23–C28, 161.6, 166.5 (C21, C22). Mass m/e (relative intensity): 602 (M+1, 45), 449 (100), 376 (40), 347 (12), 332 (15), 136 (15), 72 (46); precise mass ($C_{28}H_{20}H_5O_{11}$): found, 602.116; required 602.116.

EXAMPLE 28
20-O-phenyl-9-aminocamptothecin

To 20 ml hydrochloric acid solution (1 M), 1 g (0.0020 mol) 20-O-phenyl-9-nitrocamptothecin and 0.2 g Fe powders were added. The mixture was shaken for 30 min. The remaining Fe powders was removed by filtration. The filtrate was extracted with 100 ml methylene chloride (25 ml×4). The combined extracts were combined and dried over 5 g anhydrous sodium sulfate for 2 hr. The solvents were evaporated by a rotary evaporator. The residue was separated and purified by column chromatography with THF-Methylene chloride (1:10) as eluent. The pure product (0.6 g) was obtained as brown powders, yield 64%.

Numerous modifications and variations of the present invention are possible in light of the above teachings. It is therefore to be understood that within the scope of the appended claims, the present invention may be practiced otherwise than as specifically described herein.

What is claimed is:

1. An aromatic camptothecin ester having the structure:

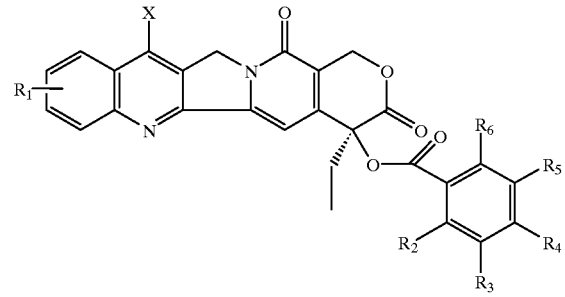

wherein $R^1$ is H, $NO_2$, $NH_2$, $N_3$, a halogen, carboxyl, a $C_{1-6}$ alkyl group, a $C_{1-6}$ alkyenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$, hydroxyl, SH, $SR^8$, a carbonyl group, a $SiR_3^{10}$; wherein the $R^1$ group is respectively positioned at the 9, 10, 1 1, or 12 position of ring A; $R^7$ is H or a $C_{1-8}$ alkyl group; n is an integer of 1 to 8; $R^8$ is a $C_{1-8}$ alkyl group or a phenyl group; $R^{10}$ is a $C_{1-4}$ alkyl group; X is H, a $C_{1-8}$ alkyl group, a $C_{1-8}$ alkenyl group, a $C_{1-8}$ alkoxyl group, an aroxyl group, a $SiR_3^{11}$ group, or $CH_2NZY$; and wherein $R^2$, $R^3$, $R^4$, $R^5$, and $R^6$ are, independently, H, $C_{1-12}$ alkyl group, $C_{1-12}$ alkenyl group, COOH, $SO_3H$, CN, $CF_3$, $CCl_3$, $CH_2F$, $CH_2Cl$, $CHF_2$, $CHCl_2$, OH, $OR^{12}$, $N_3$, $NO_2$, $NR_2^{13}$, carbonyl group, halogen, wherein $R^{11}$ is a $C_{1-4}$ alkyl group; Z and Y are, independently, H, $C_{1-4}$ alkyl, or a $C_{1-4}$ halogenated alkyl group; $R^{12}$ is a $C_{1-8}$ alkyl group, a $C_{1-8}$ alkenyl group, or an aromatic group; and wherein $R^{13}$ is H or $C_{1-4}$ alkyl group, wherein at least one of $R^2$, $R^3$, $R^4$, $R^5$, or $R^6$ is a substituent other than hydrogen, and wherein at least two of $R^2$, $R^3$, $R^4$, $R^5$, or $R^6$ is hydrogen.

2. A pharmaceutical composition comprising an effective amount of at least one aromatic camptothecin ester of claim 1 and at least one pharmaceutically acceptable carrier or diluent.

3. The aromatic camptothecin ester of claim 1, wherein $R^1$ is hydrogen and X is hydrogen.

4. The aromatic camptothecin ester of claim 3, wherein $R^2=R^3=R^4=R^5=R^6=H$.

5. The aromatic camptothecin ester of claim 3, wherein $R^2=R^3=R^5=R^6=H$, $R^4=CF_3$.
6. The aromatic camptothecin ester of claim 3, wherein $R^2=R^3=R^4=R^6=H$, $R^5=CF_3$.
7. The aromatic camptothecin ester of claim 3, wherein $R^2=R^3=R^4=R^5=H$, $R^6=CF_3$.
8. The aromatic camptothecin ester of claim 3, wherein $R^2=R^3=R^6=H$, $R^4=R^5=NO_2$.
9. The aromatic camptothecin ester of claim 3, wherein $R^2=R^4=R^6=H$, $R^3=R^5=NO_2$.
10. The aromatic camptothecin ester of claim 3, wherein $R^2=R^3=R^5=H$, $R^4=R^6=NO_2$.
11. The aromatic camptothecin ester of claim 3, wherein $R^2=R^3=R^5=R^6=H$, $R^4=NO_2$.
12. The aromatic camptothecin ester of claim 3, wherein $R^2=R^3=R^4R^6=H$, $R^5=NO_2$.
13. The aromatic camptothecin ester of claim 3, wherein $R^3=R^4=R^5=R^6=H$, $R^2=NO_2$.
14. The aromatic camptothecin ester of claim 3, wherein $R^3=R^4=R^5=R^6=H$, $R^2=CN$.
15. The aromatic camptothecin ester of claim 3, wherein $R^2=R^3=R^4=R^6=H$, $R^5=CN$.
16. The aromatic camptothecin ester of claim 3, wherein $R^2=R^3=R^5=R^6=H$, $R^4=CN$.
17. The aromatic camptothecin ester of claim 3, wherein $R^3=R^4=R^5=R^6=H$, $R^2=F$.
18. The aromatic camptothecin ester of claim 3, wherein $R^2=R^3=R^4=R^6=H$, $R^5=F$.
19. The aromatic camptothecin ester of claim 3, wherein $R^2=R^3=R^5=R^6=H$, $R^4=F$.
20. The aromatic camptothecin ester of claim 3, wherein $R^3=R^4=R^5=R^6=H$, $R^2=Cl$.
21. The aromatic camptothecin ester of claim 3, where $R^2=R^3=R^4=R^6=H$, $R^5=Cl$.
22. The aromatic camptothecin ester of claim 3, wherein $R^2=R^3=R^5=R^6=H$, $R^4=Cl$.
23. The aromatic camptothecin ester of claim 3, wherein $R^3=R^4=R^5=R^6=H$, $R^2=Br$.
24. The aromatic camptothecin ester of claim 3, wherein $R^2=R^3=R^4=R^6=H$, $R^5=Br$.
25. The aromatic camptothecin ester of claim 3, wherein $R^2=R^3=R^5=R^6=H$, $R^4=Br$.
26. The aromatic camptothecin ester of claim 3, wherein $R^3=R^4=R^5=R^6=H$, $R^2=OH$.
27. The aromatic camptothecin ester of claim 3, wherein $R^2=R^3=R^4=R^6=H$, $R^5=OH$.
28. The aromatic camptothecin ester of claim 3, wherein $R^2=R^3=R^5=R^6=H$, $R^4=OH$.
29. The aromatic camptothecin ester of claim 1, where $R^1$ is 9-$NO_2$, and X is H.
30. The aromatic camptothecin ester of claim 29, wherein $R^2=R^3=R^4=R^5=R^6=H$.
31. The aromatic camptothecin ester of claim 29, wherein $R^2=R^3=R^5=R^6=H$, $R^4=CF_3$.
32. The aromatic camptothecin ester of claim 29, wherein $R^2=R^3=R^4=R^6=H$, $R^5=CF_3$.
33. The aromatic camptothecin ester of claim 29, wherein $R^2=R^3=R^4=R^5=H$, $R^6=CF_3$.
34. The aromatic camptothecin ester of claim 29, wherein $R^2=R^3=R^6=H$, $R^4=R^5=NO_2$.
35. The aromatic camptothecin ester of claim 29, wherein $R^2=R^4=R^6=H$, $R^3=R^5=NO_2$.
36. The aromatic camptothecin ester of claim 29, wherein $R^2=R^3=R^5=H$, $R^4=R^6=NO_2$.
37. The aromatic camptothecin ester of claim 29, wherein $R^2=R^3=R^5=R^6=H$, $R^4=N_2$.
38. The aromatic camptothecin ester of claim 29, wherein $R^2=R^3=R^4=R^6=H$, $R^5=NO_2$.
39. The aromatic camptothecin ester of claim 29, wherein $R^3=R^4=R^5=R^6=H$, $R^2=NO_2$.
40. The aromatic camptothecin ester of claim 29, wherein $R^3=R^4=R^5=R^6=H$, $R^2=CN$.
41. The aromatic camptothecin ester of claim 29, wherein $R^2=R^3=R^4=R^6=H$, $R^5=CN$.
42. The aromatic camptothecin ester of claim 29, wherein $R^2=R^3=R^5=R^6=H$, $R^4=CN$.
43. The aromatic camptothecin ester of claim 29, wherein $R^3=R^4=R^5=R^6=H$, $R^2=F$.
44. The aromatic camptothecin ester of claim 29, wherein $R^2=R^3=R^4=R^6=H$, $R^5=F$.
45. The aromatic camptothecin ester of claim 29, wherein $R^2=R^3=R^5=R^6=H$, $R^4=F$.
46. The aromatic camptothecin ester of claim 29, wherein $R^3=R^4=R^5=R^6=H$, $R^2=Cl$.
47. The aromatic camptothecin ester of claim 29, where $R^2=R^3=R^4=R^6=H$, $R^5=Cl$.
48. The aromatic camptothecin ester of claim 29, wherein $R^2=R^3=R^5=R^6=H$, $R^4=Cl$.
49. The aromatic camptothecin ester of claim 29, wherein $R^3=R^4=R^5=R^6=H$, $R^2=Br$.
50. The aromatic camptothecin ester of claim 29, wherein $R^2=R^3=R^4=R^6=H$, $R^5=Br$.
51. The aromatic camptothecin ester of claim 29, wherein $R^2=R^3=R^5=R^6=H$, $R^4=Br$.
52. The aromatic camptothecin ester of claim, 29, wherein $R^2=R^6=H$, $R^3=R^5=NO_2$, $R^4=CH_3$.
53. The aromatic camptothecin ester of claim 29, wherein $R^3=R^4=R^5=R^6=H$, $R^2=OH$.
54. The aromatic camptothecin ester of claim 29, wherein $R^2=R^3=R^4=R^6=H$, $R^5=OH$.
55. The aromatic camptothecin ester of claim 29, wherein $R^2=R^3=R^5=H$, $R^4=OH$.
56. The aromatic camptothecin ester of claim 1, wherein $R^1$ is 9-$NH_2$, X is H.
57. The aromatic camptothecin ester of claim 56, wherein $R^2=R^3=R^4=R^5=R^6=H$.
58. The aromatic camptothecin ester of claim 56, wherein $R^2=R^3=R^5=R^6=H$, $R^4=CF_3$.
59. The aromatic camptothecin ester of claim 56, wherein $R^2=R^3=R^4=R^6=H$, $R^5=CF_3$.
60. The aromatic camptothecin ester of claim 56, wherein $R^2=R^3=R^4=R^5=H$, $R^6=CF_3$.
61. The aromatic camptothecin ester of claim 56, wherein $R^2=R^3=R^6=H$, $R^4=R^5=NO_2$.
62. The aromatic camptothecin ester of claim 56, wherein $R^2=R^4=R^6=H$, $R^3=R^5=NO_2$.
63. The aromatic camptothecin ester of claim 56, wherein $R^2=R^3=R^5=H$, $R^4=R^6=NO_2$.
64. The aromatic camptothecin ester of claim 56, wherein $R^2=R^3=R^5=R^6=H$, $R^4=NO_2$.
65. The aromatic camptothecin ester of claim 56, wherein $R^2=R^3=R^4=R^6=H$, $R^5=NO_2$.
66. The aromatic camptothecin ester of claim 56, wherein $R^3=R^4=R^5=R^6=H$, $R^2=NO_2$.
67. The aromatic camptothecin ester of claim 56, wherein $R^3=R^4=R^5=R^6=H$, $R^2=CN$.
68. The aromatic camptothecin ester of claim 56, wherein $R^2=R^3=R^4=R^4=R^6=J$. $R^5=CN$.
69. The aromatic camptothecin ester of claim 56, wherein $R^2=R^3=R^4=R^6=H$, $R^5=CN$.
70. The aromatic camptothecin ester of claim 56, wherein $R^3=R^4=R^5=R^6=H$, $R^4=F$.
71. The aromatic camptothecin ester of claim 56, wherein $R^2=R^3=R^4=R^6=H$, $R^5=F$.
72. The aromatic camptothecin ester of claim 56, wherein $R^2=R^3=R^5=R^6=H$, $R^4=F$.

73. The aromatic camptothecin ester of claim 56, wherein $R^3=R^3=R^5=R^6=H$, $R^2=Cl$.

74. The aromatic camptothecin ester of claim 56, wherein $R^2=R^3=R^4=R^6=H$, $R^5=Cl$.

75. The aromatic camptothecin ester of claim 56, wherein $R^2=R^3=R^5=R^6=H$, $R^4=Cl$.

76. The aromatic camptothecin ester of claim 56, wherein $R^3=R^4=R^5=R^6=H$, $R^2=Br$.

77. The aromatic camptothecin ester of claim 56, wherein $R^2=R^3=R^4=R^6=H$, $R^5=Br$.

78. The aromatic camptothecin ester of claim 56, wherein $R^2=R^3=R^5=R^6=H$, $R^4=Br$.

79. The aromatic camptothecin ester of claim 56, wherein $R^3=R^4=R^5=R^6=H$, $R^2=OH$.

80. The aromatic camptothecin ester of claim 56, wherein $R^2=R^3=R^4=R^6=H$, $R^5=OH$.

81. The aromatic camptothecin ester of claim 56, wherein $R^2=R^3=R^5=R^6=H$, $R^4=OH$.

82. The aromatic camptothecin ester of claim 1, wherein said carbonyl has the formula $COR^9$, wherein, $R^9$ represents a $C_{1-8}$ alkyl group or a phenyl group.

83. The aromatic camptothecin ester of claim 82, wherein said phenyl group is substituted.

84. The aromatic camptothecin ester of claim 1, wherein said $R^1$ is a disubstituted 10, 11-O—$(CH_2)_y$—O— group wherein y is an integer of from 1 to 3.

85. A method to inhibit the enzyme topoisomerase I comprising administering a composition comprising at least one aromatic camptothecin ester of claim 1.

86. A method to treat cancer in a patient comprising administering a composition comprising at least one aromatic camptothecin ester of claim 1 to said patient in an effective amount to treat said cancer.

87. The method of claim 86, wherein said cancer is lung, breast, colon, prostate, melanoma, pancreas, stomach, liver, brain, kidney, uterus, cervix, ovaries, urinary track, gastrointestinal, or leukemia.

88. The method of claim 86, wherein said composition is administered orally.

89. The method of claim 86, wherein said composition is administered intramuscularly.

90. The method of claim 86, wherein said composition is administered transdermally.

91. The method of claim 86, wherein said cancer is a solid tumor.

92. The method of claim 86, wherein said cancer is a blood borne tumor.

93. The method of claim 86, wherein said c omp ositi on is a liposome containing said at least one aromatic camptothecin compound.

94. The method of claim 86, wherein said composition is administered by an airborne delivery system.

95. An (S)-aromatic camptothecin ester having the structure:

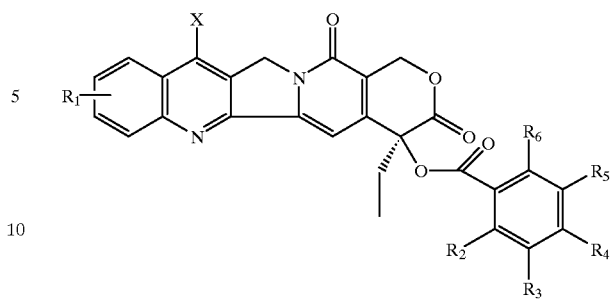

wherein $R^1$ is H, $NO_2$, $NH_2$, $N_3$, a halogen, carboxyl, a $C_{1-16}$ alkyl group, a $C_{1-16}$ alkyenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$, hydroxyl, SH, $SR^8$, a carbonyl group, a $SiR^{310}$; wherein the $R^1$ group is respectively positioned at the 9, 10, 11, or 12 position of ring A; $R^7$ is H or a $C_{1-8}$ alkyl group; n is an integer of 1 to 8; $R^8$ is a $C_{1-8}$ alkyl group or a phenyl group; $R^{10}$ is a $C_{1-4}$ alkyl group; X is H, a $C_{1-8}$ alkyl group, a $C_{1-8}$ alkenyl group, a $C_{1-8}$ alkoxyl group, an aroxyl group, a $SiR_3^{11}$ group, or $CH_2NZY$; and wherein $R^2$, $R^3$, $R^4$, $R^5$, and $R^6$ are, independently, H, $C_{1-12}$ alkyl group, $C_{1-12}$ alkenyl group, COOH, $SO_3H$, CN, $CF_3$, $CCl_3$, $CH_2F$, $CH_2Cl$, $CHF_2$, $CHCl_2$, OH, $OR^{12}$, $N_3$, $NO_2$, $NR_2^{13}$, carbonyl group, halogen, wherein $R^{11}$ is a $C_{1-4}$ alkyl group; Z and Y are, independently, H, $C_{1-4}$ alkyl, or a $C_{1-4}$ halogenated alkyl group; $R^{12}$ is a $C_{1-8}$ alkyl group, a $C_{1-8}$ alkenyl group, or an aromatic group; and wherein $R^{13}$ is H or $C_{1-4}$ alkyl group, and wherein at least one of $R^2$, $R^3$ $R^4$, $R^5$, or $R^6$ is a substituent other than hydrogen and at least two of $R^2$, $R^3$, $R^4$, $R^5$, or $R^6$ is hydrogen.

96. A pharmaceutical composition comprising an effective amount of at least one aromatic camptothecin ester of claim 95 and at least one pharmaceutically acceptable carrier or diluent.

97. The aromatic camptothecin ester of claim 95, wherein $R^2=R^3=R^4=R^5=R^6=H$.

98. A method to inhibit the enzyme topoisomerase I comprising administering a composition comprising at least one aromatic camptothecin ester of claim 95.

99. A method to treat cancer in a patient comprising administering a composition comprising at least one aromatic camptothecin ester of claim 95 to said patient in an effective amount to treat said cancer.

100. The method of claim 95, wherein said cancer is lung, breast, colon, prostate, melanoma, pancreas, stomach, liver, brain, kidney, uterus, cervix, ovaries, urinary track, gastrointestinal, or leukemia.

101. The method of claim 95, wherein said composition is administered orally.

102. The method of claim 95, wherein said composition is administered intramuscularly.

103. The method of claim 95, wherein said composition is administered transdermally.

104. The method of claim 95, wherein said cancer is a solid tumor.

105. The method of claim 95, wherein said cancer is a blood borne tumor.

106. The method of claim 95, wherein said composition is a liposome containing said at least one aromatic camptothecin compound.

107. The method of claim 95, wherein said composition is administered by an airborne delivery system.

* * * * *

UNITED STATES PATENT AND TRADEMARK OFFICE
CERTIFICATE OF CORRECTION

PATENT NO.    : 6,228,855 B1
DATED         : May 8, 2001
INVENTOR(S)   : Cao et al.

It is certified that error appears in the above-identified patent and that said Letters Patent is hereby corrected as shown below:

Column 22,
Line 59, after "hydrogen", insert -- and when "$R^2$, $R^3$, $R^6$ and $R^6$ are hydrogens, $R^4$ is not $No_2$ --

Column 24,
Line 33, $R^2=R^3=R^5=H$" should read -- $R^2=R^3=R^5=R^6=H$ --
Line 59, "$R^2=R^3=R^4=R^4=R^6=J$" should read -- $R^2=R^3=R^4=R^6=H$ --

Column 26,
Line 19, "$SiR^{310}$" should read -- $SiR_3^{10}$ --; and
Line 34, after "hydrogen", insert -- and when "$R^2$, $R^3$, $R^5$ and $R^6$ are hydrogens, $R^4$ is not $NO_2$ --

Signed and Sealed this

Twenty-fourth Day of June, 2003

JAMES E. ROGAN
*Director of the United States Patent and Trademark Office*